United States Patent [19]

Doyon et al.

[11] Patent Number: 5,283,065
[45] Date of Patent: Feb. 1, 1994

[54] CONTROLLED RELEASE PHARMACEUTICAL COMPOSITIONS FROM SPHERICAL GRANULES IN TABLETTED ORAL DOSAGE UNIT FORM

[75] Inventors: Daniel J. Doyon, Florida; Madurai G. Ganesan; Wendy A. Preston, both of Suffern; Nitin V. Sheth, Middletown, all of N.Y.

[73] Assignee: American Cyanamid Company, Stamford, Conn.

[21] Appl. No.: 859,617

[22] Filed: Mar. 23, 1992

Related U.S. Application Data

[63] Continuation of Ser. No. 410,707, Sep. 21, 1989, abandoned.

[51] Int. Cl.$^5$ .......................... A61K 9/14; A61K 9/44; A61K 9/52
[52] U.S. Cl. .................. 424/467; 424/472; 424/474; 424/465; 424/468; 424/469; 424/480; 424/482; 424/484; 424/489; 424/494; 424/497
[58] Field of Search ............... 424/489, 468, 469, 470, 424/482, 499, 490, 494

[56] References Cited

U.S. PATENT DOCUMENTS

| | | | |
|---|---|---|---|
| 2,687,367 | 8/1954 | Burrin | 424/470 |
| 2,887,436 | 5/1959 | Klioze | 424/470 |
| 2,953,497 | 9/1960 | Press | 424/470 |
| 3,080,294 | 3/1963 | Shepard | 167/82 |
| 3,115,441 | 12/1963 | Hermelin | 167/82 |
| 3,344,029 | 9/1967 | Berger | 424/470 |
| 3,865,935 | 2/1975 | Amann | 424/181 |
| 4,012,498 | 3/1977 | Kornblum | 424/470 |
| 4,173,626 | 11/1979 | Dempski et al. | 424/19 |
| 4,177,254 | 12/1979 | Khan | 424/489 |
| 4,353,887 | 10/1982 | Hess et al. | 424/15 |
| 4,444,769 | 4/1984 | Blume | 424/470 |
| 4,483,847 | 11/1984 | Augart | 424/470 |
| 4,572,833 | 2/1986 | Pedersen | 424/470 |
| 4,606,909 | 8/1986 | Bechgaard et al. | 424/21 |
| 4,784,858 | 11/1988 | Ventouras | 424/468 |
| 4,808,413 | 2/1989 | Joshi | 424/489 |
| 4,837,030 | 6/1989 | Valorose, Jr. et al. | 424/489 |
| 4,844,910 | 7/1989 | Leslie et al. | 424/470 |
| 4,853,229 | 8/1989 | Theeuwes | 424/490 |
| 4,880,830 | 11/1989 | Rhodes | 424/468 |

FOREIGN PATENT DOCUMENTS

| | | |
|---|---|---|
| 2041222 | 9/1980 | United Kingdom . |
| 1598458 | 9/1981 | United Kingdom . |
| 2202143 | 9/1988 | United Kingdom . |

Primary Examiner—Thurman K. Page
Assistant Examiner—James M. Spear
Attorney, Agent, or Firm—H. G. Jackson; James V. Costigan

[57] ABSTRACT

A controlled release pharmaceutical composition in oral dosage unit form comprising a tablet comprising a therapeutically effective number of active spherical granules comprising an effective amount of active medicament, a pharmaceutically acceptable normally solid diluent adapted to form a diffusable matrix for the active medicament and an optional pharmaceutically acceptable excipient; and a number of compressible spherical granules comprising a mono- or di-saccharide, an optional pharmaceutically acceptable normally solid diluent adapted to form a diffusable matrix, an optional active medicament and/or an optional pharmaceutically acceptable excipient wherein the average compressive yield of the compressible spherical granules is less than the average compressive yield of the active spherical granules is provided. A method for the preparation and for the administration of the above defined composition is provided as well.

45 Claims, 16 Drawing Sheets

CONTROLLED RELEASE PHARMACEUTICAL COMPOSITIONS FROM SPHERICAL GRANULES IN TABLETTED ORAL DOSAGE UNIT FORM

This application is a continuation of 07/410,707 filed Sep. 21, 1989 now abandoned.

FIELD OF THE INVENTION

The invention relates to controlled release pharmaceutical compositions in oral dosage units comprising blends of active spherical granules and compressible spherical granules, which may or may not contain active medicament, formed into tablets; to a method for controlling the release of an active medicament in the blood stream of a warm-blooded mammal; and to a method for the preparation of the foregoing tabletted oral dosage unit. Coated tabletted oral dosage units, scored tabletted oral dosage units and tabletted oral dosage units which contain multiple medicaments are also provided.

These tabletted oral dosage units provide excellent controlled release of the active medicament being delivered and uniform active medicament dosage from tablet to tablet. Although they are effective at a broad range of dosages of active medicament, they are particularly effective when comprised of relatively low dosage ranges of active medicament. Additionally, they can be stored for prolonged periods of time at a wide range of temperatures and humidities while retaining their potency and controlled release properties.

BACKGROUND OF THE INVENTION

It is often important to control the release of an active medicament to achieve a slow release of the medicament over a prolonged period of time extending the duration of the action of the medicament over that achieved by conventional delivery. Many active medicaments in traditional pharmaceutical forms require frequent ingestion of multiple unit doses per day resulting in wide variations in serum concentration throughout the course of treatment and poor patient compliance.

Dempski, et al, U.S. Pat. No. 4,173,626, disclose capsules comprising uncoated indomethacin pellets for immediaterelease, coated indomethacin pellets for prolonged release, and non-medicated pellets as volume fill.

The incorporation of water-insoluble medicament contained in spheroids comprised of microcrystalline cellulose and at least one cellulose derivative into capsules, sachets and cachets is disclosed in U.K. Patent Publication No. GB 2202143.

Concurrently filed, copending U.S. patent application, discloses hard shell capsules filled with carbonic anhydrase inhibitor containing active spherical granules.

Capsules, however, have many drawbacks such as the inability of certain people to swallow capsules, the inability to be divided, and instability. Additionally, capsules are subject to tampering, are relatively hard to manufacture and are relatively expensive to manufacture.

Shepard, U.S. Pat. No. 3,080,294, discloses a sustained release pharmaceutical-tablet comprising an inner core coated with multiple layers of an active medicament mixture, each layer releasing a portion of active medicament as it is successively dissolved. Variations in such coatings result in a lack of uniformity among tablets, and crushing or dividing of the tablet exposes many layers of active medicament resulting in simultaneous release of the active medicament of each layer. The coatings do not encapsulate the medicament.

Amann, U.S. Pat. No. 3,865,935, discloses erythromycin tablets which are stable outside the stomach but which produce immediate action upon disintegration in the stomach. These tablets require sodium citrate or sodium citrate dihydrate and do not yield a controlled release of prolonged duration.

In U.S. Pat. No. 3,115,441, Hermelin discloses irregularly shaped coated analgesic particles in a compressed matrix of the same analgesic.

U.K. Patent Specification No. GB 1,598,458 discloses tablets of brittle microcapsules and other particles with brittle coatings, particularly potassium chloride, with 2 to 20 percent by weight of brittle microcapsules or brittle particles of a water-soluble, natural or synthetic wax which forms a matrix in which the particles are suspended. The tablets must, in a major portion, comprise the active medicament and are particularly deficient in lower dosages.

U.K. Patent Publication No. GB 2,041,222 discloses the tabletting of microcapsules of indoprofen. Other active medicaments may be included in the tablet. The compression of a single type of microcapsules results in crushing of the microcapsule and consequently, the loss of controlled release properties. These tablets are only suitable for high dosage delivery as well because the entire tablet is formed of microcapsules containing active medicament. Additionally, the microcapsules are not formed by spheronization.

Hess, et al, U.S. Pat. No. 4,353,887, discloses a divisible tablet comprising active granules wherein the surface area of the tablet is not materially increased by division.

In Bechgaard, et al, U.S. Pat. No. 4,606,909, the placement of a sparingly soluble active substance such as tetracycline in an oral controlled release dosage form is disclosed.

In Ventouras, U.S. Pat. No. 4,784,858, a controlled release tablet comprising (1) coated cores, not necessarily spheronized, comprising a core of a water-soluble pharmaceutically active substance dispersed in a water-insoluble polymeric excipient and a swellable water-insoluble polymeric substance; and (2) a coating of an elastic, water insoluble and semipermeable diffusion film of a polymer. Here, the core is made to expand with water causing the surface of the coating to extend, making it permeable, and thereby releasing the medicament in the core.

Valorose et al, U.S. Pat. No. 4,837,030, disclose tablets for the controlled release of tetracycline compounds comprising active spherical granules.

Concurrently filed copending application, Ser. No. 031,065, discloses two pulse pharmaceutical delivery systems for 7-dimethylamino-6-deoxy-6-demethyltetracycline or non-toxic acid addition salts thereof comprising initial loading components and pH sensitive polymer coated secondary loading components adapted to provide therapeutically effect blood concentrations of minocycline for up to about 24 hours in a once-a-day dosage.

FIG. 1 is a micrograph of K-Dur ® potassium chloride tablets from Key Pharmaceuticals. The potassium chloride granules (1) are distributed throughout a tablet matrix (3) comprising powdered and/or granular material.

FIG. 2 is a micrograph of PCE ® erythromycin tablets from Abbott Laboratories. The erythromycin granules (5) are distributed throughout a tablet matrix (7) comprising powdered and/or granular material.

FIG. 3 is a micrograph of Theo-Dur ® theophylline anhydrous tablets from Key Pharmaceuticals. The theophylline anhydrous granules (9) are distributed throughout a tablet matrix (11) comprising powdered and/or granular material.

All of these tablets have the disadvantages discussed above including crushing of the active particles with resultant loss of controlled release properties. Furthermore, commercial production of tablets at low dosages according to the prior art is impractical and results in great variability in actual dosages and relatively large tablets.

It has now been discovered that the controlled release properties of active spherical granules can be protected and low dosage oral dosage unit forms can be prepared if the active spherical granules are tabletted with a number of compressible spherical granules which deform or crack at compressible yields lower than the active spherical granules, and therefore before the active spherical granules, sufficiently to cushion the active spherical granules and fill at least a portion of the voids normally created during tabletting. These tablets can be formed into various configurations making them suitable for virtually all orally administered active medicaments and treatments in which controlled release is desirable. Additionally, they are stable, retaining their potency and controlled release properties under a wide range of storage conditions.

SUMMARY OF THE INVENTION

Figure 1:
FIG. 1 is a micrograph of a K-Dur ® tablet from Key Pharmaceuticals.
Figure 2:
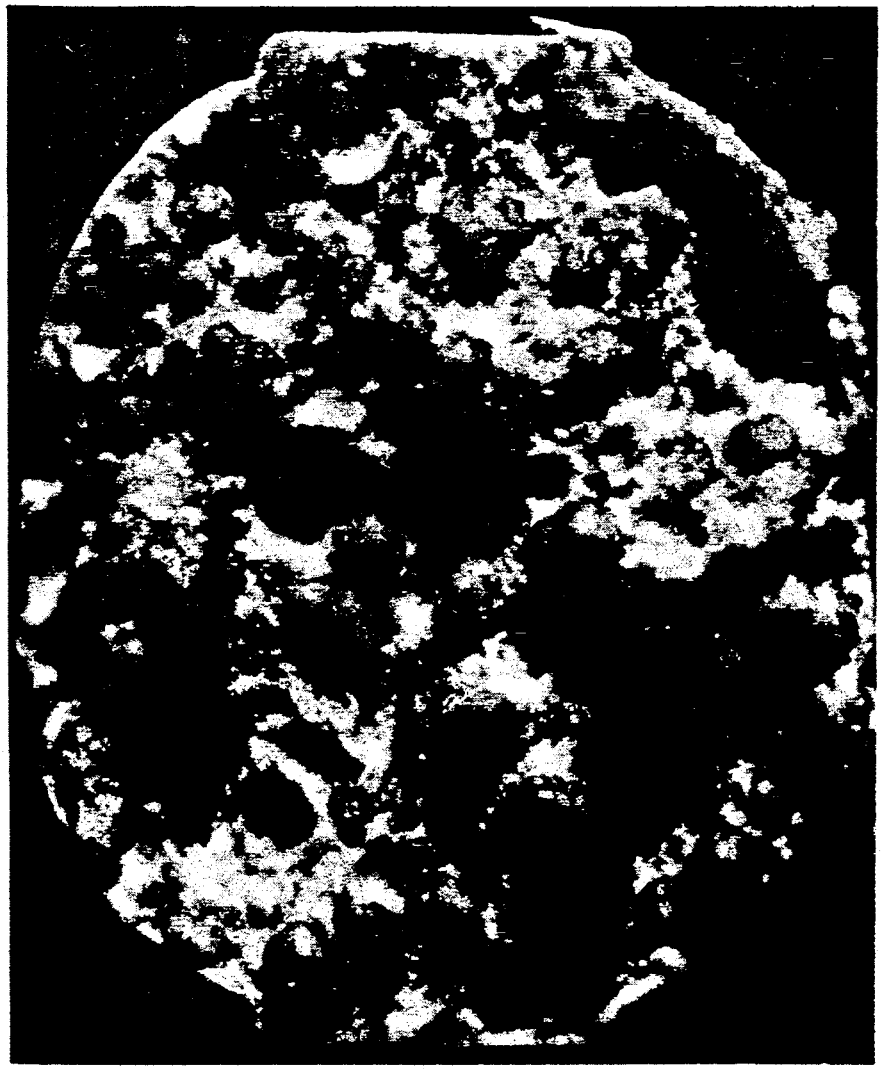
FIG. 2 is a micrograph of a PCE ® tablet from Abbott Laboratories.
Figure 3:
FIG. 3 is a micrograph of a Theo-Dur ® tablet from Key Pharmaceuticals.

According to the present invention, there are provided controlled release pharmaceutical compositions comprising a tablet comprising (A) a therapeutically effective number of active spherical granules which comprise (i) an effective amount of at least one active medicament, (ii) a pharmaceutically acceptable normally solid diluent adapted to form a diffusable matrix for the active medicament(s), and optionally, (iii) at least one pharmaceutically acceptable excipient which may be the same as or different than (A)(ii); and (B) a number of compressible spherical granules comprising (i) at least one mono- or di-saccharide, optionally; (ii) a pharmaceutically acceptable normally solid diluent adapted to form a diffusable matrix which may be the same as or different than (A)(ii); optionally, (iii) an effective amount of at least one active medicament which may be the same as or different than (A)(i); optionally (iv) at least one pharmaceutically acceptable excipient other than a mono- or di-saccharide which may be the same as or different than (A)(ii), (A)(iii) or (B)(ii); or optionally (v) a combination of any of (B)(ii), (B)(iii), and (B)(iv); wherein the average compressive yield of component (B) is less than the average compressive yield of component (A).

The invention further contemplates oral dosage units in the form of tablets which contain two different types of active spherical granules (A-1) and (A-2), each of which contains at least one different active medicament.

The invention also provides a method for controlling the release of at least one active medicament in the blood stream of a warm-blooded mammal over a prolonged period of time comprising the ingestion of one or more oral dosage unit tablets as described above, as well as a method for the preparation of a pharmaceutical composition in oral dosage unit form comprising a tablet comprising the steps of (a) blending (i) an effective amount of at least one active medicament, (ii) a pharmaceutically acceptable normally solid diluent adaptable to form a diffusable matrix for the at least one active medicament (a)(i), and optionally, (iii) at least one pharmaceutically acceptable excipient which may be the same as or different than (a)(ii); (b) independently blending (i) at least one mono- or di-saccharide, optionally, (ii) a pharmaceutically acceptable normally solid diluent adaptable to form a diffusable matrix which may be the same as or different than (a)(ii), optionally, (iii) an effective amount of at least one active medicament which may be the same as or different than (a)(i), optionally (iv) at least one pharmaceutically acceptable excipient other than a mono- or di-saccharide which may be the same as or different than either (a)(ii), (a)(iii), or (b)(ii); or optionally, (v) a combination of any of (b)(ii), (b)(iii) and (b)(iv); (c) independently granulating the resultant blends of steps (a) and (b) in the presence of a granulating liquid; (d) independently extruding the resultant granulates of step (c); (e) independently spheronizing the resultant extrudates of step (d) to form active spherical granules (A) derived from step (a) and compressible spherical granules (B) derived from step (b) so that the average compressive yield of component (B) is less than the average compressive yield of component (A); (f) drying components (A) and (B); (g) optionally adding a lubricant; and (h) forming a tablet from a blend of a therapeutically effective number of active spherical granules (A) and a number of compressible spherical granules (B).

The tabletted unit dosage forms described above provide uniform active medicament content from tablet to tablet and are well adapted for the formulation and administration of a wide range of dosages or amounts of active medicament tablets and particularly relatively low dosages and amounts. They provide a controlled release and a longer release of active medicaments which prolongs the effects of the active medicaments resulting in the administration of relatively low total amounts of active medicament and less frequent administrations to a subject. They avoid high local concentrations in a system which may cause side effects such as gastroirritability and are stable, retaining their potency and their controlled release properties in a broad spectrum of storage conditions.

DETAILED DESCRIPTION OF THE INVENTION

A novel controlled release pharmaceutical composition in oral dosage unit form has been discovered comprising a tablet comprising a therapeutically effective number of active spherical granules and a number of compressible spherical granules. Many benefits can be realized from this novel oral dosage unit form over other conventional unit dosage forms which incorporate only one type of spherical granules. For example, the controlled release tablet disintegrates quickly freeing the active spherical granules which in turn release the active medicament at a predetermined rate. The compressible spherical granules in the tablet distort or crack and fill voids to provide the desired cushion to prevent the active spherical granules from breaking during the tabletting process thereby guarding against any loss of the controlled release properties of the active spherical granules. This results in a superior controlled delivery of active medicament to a subject which results in the ability of relatively low dosages o active medicament in the oral dosage unit form to sustain a desired blood level in a subject for a relatively long period of time. Therefore, less frequent administration of the active medicament to a subject and better subject compliance with a medicament regimen is possible.

The compressible spherical granules also aid in achieving the desired tablet weight, size or configuration and can provide additional, supplemental or immediately active medicament loading which results in one oral dosage unit containing both a loading dose and a slow release dose of at least one active medicament.

The present invention is widely applicable to a number of active medicaments. Multiple active medicaments can be delivered in a single oral unit dosage form as well.

Further advantages of the invention are achieved by processing onto the tablets or onto any of the spherical granules, one or more film coatings which can further modify the properties of the tablets such as release rates, disintegration rates, taste, texture, color, physical appearance and the like.

Oral dosage unit forms are those which are orally administered and contain active medicaments which are absorbed into the blood stream from the alimentary tract.

A therapeutically effective number of active spherical granules is that number which delivers and maintains a recommended dosage or concentration level of a particular active medicament to the blood stream or plasma of a subject within a recommended period of time and maintains that level or a further recommended level for a further recommended period of time. Such an amount will depend upon the active medicament prescribed and the age, weight, sex, sensitivity and the like of the individual subject.

The number of compressible spherical granules in the tablet should be at least a number sufficient to cushion at least a therapeutically effective number of active spherical granules against the effects of any compression used in forming the tablet. It is essential that the average compressive yield of the compressible spherical granules is less than the average compressive yield of the active spherical granules, thereby allowing the compressible spherical granules to cushion the active spherical granules during compression and to fill voids during tabletting. If the active spherical granules were of the same or lower compressive yield as the compressible spherical granules, the active spherical granules would crack or deform and lose their controlled release properties. The active spherical granules need not be incompressible but are distinguished from the compressible spherical granules in that they will not compress at as low a compressive yield as the compressible spherical granules.

Figure 4:
FIG. 4 is a micrograph of a methazolamide tablet of the present invention.

FIG. 4 is a micrograph of Neptazane ® (Lederle Laboratories) methazolamide tablets according to the present invention. Substantially unbroken active spherical granules (13) are evenly dispersed with compressible spherical granules (15).

Active medicaments with varying solubility in water, from sparingly soluble to soluble, are useful in the present invention. Among the active medicaments useful in the present invention are ACE inhibitors, aminoglycocides, analgesics, antiarrhythmics, antibacterial agents, antibiotics, anticancer agents, antidepressants, antidiabetics, antiepileptics, antifungical agents, antihistamines, antihypertensives, antiinflammatories (steroidal and non-steroidal), antinauseants, antiprostaglandins, antirheumatics, antiseptics, barbituates, beta blockers, betalactamase inhibitors, bronchodialators, calcium channel blockers, cardiac glycosides, cephalosporins, diuretics, hormones, immune reagents, immunostimulatory agents, immuno-suppressive agents, liposaccharide complexing agents, methylxanthines, minerals, muscle relaxants, nutritional agents, O-beta-hydroxyethylated rutins, propoxyphenes, quinolones, salicylates, sedatives, tetracycline compounds, tissue growth factors, tranquilizers, vasodilators, vitamins and the like, or mixture of any of the foregoing. Such active medicaments include without limitation acetaminophen, acetazolamide, acetophenetidin, acetylsalcylic acid, achromycin hydrochloride, amilorid, benzocaine, bendrofluazide, benzthiazide, betamethasone, calcium and salts thereof including leucovorin calcium, carbamazepine, clindamycin chlorpropamide, chlorothalidone, chlorothiazide, clofibrate, cortisone acetate, cyclopenthiazide, dexamethazone, dextroamphetamine sulfate, diclofenac sodium, digoxin, dimethindene and salts thereof, di- prophylline, disopyramide and salts thereof, dipyrone, doxycycline, embonate, erythromycin, estradiol, fenbufen, fenoprofen, ferrous fumarate, flurbiprofen, frusemide, furosemide, glibenclamide, haloperidol, hydralazine, hydrochloride, hydrochlorothiazide, hydrocortisone, hydroflumethiazide, ibuprofen, indomethacin, indoprofen, iron salts, kanamycin, ketoprofen, L-Dopa, lithium salts, metaclopramide, methazolamide, methotrexate, methotrexate sodium, methyldopa, metronidazole, minocycline hydrochloride, mofebutazone, morphine, naproxen, nifedipine, oxyphenbutazone, penicillin, peridinol and salts thereof, phenylbutazone, phenobarbital, phenylpropanolamine hydrochloride, phenytoin, pindolol, piroxicam, pirprofen, potassium chloride, prazosin, propanolol, prednisone, progesterone, proxyphilline, pyrvinium embonate, quinidine, reserpine, salicylamide, salicyl salicylic acid, sodium fluoride, spironolactone, sulfadiazine, sulfamerazine, testosterone, tetracycline compounds, theophylline, tolbutamide, trihexyphenidyl hydrochloride, trimethoprim, valproic acid, vancomycin, verapamil, zoxazolamine, or mixtures thereof.

Although this wide variety of active medicaments is suitable for use in the present invention, active medicaments which are soluble in the fluids of the alimentary tract are preferred. Special mention is made of methazolamide, ibuprofen, disopyramide phosphate, tetracycline compounds including minocycline hydrochloride, and the like.

Methazolamide, U.S. Pat. No. 2,783,241, is a carbonic anhydrase inhibitor which is useful in the treatment of chronic simple glaucoma and secondary glaucoma, and is prescribed preoperatively in acute angle closure glaucoma where the delay of surgery is desired in order to lower intraoccular pressure. It is presently available under the tradename Neptazane ® from Lederle Laboratories (PDR 43rd Ed.). It is typically administered in dosages of about 50 mg to about 100 mg two to three times daily for a normal adult human being. Oral dosage units typically comprise from about 25 mg to about 75 mg of methazolamide.

Preferably, the unit dosage forms of the present invention will release not more than about 50 percent of the methazolamide from the active spherical granules in about 1 hour and not less than about 75 percent of the methazolamide from the active spherical granules in about 12 hours when suspended in pH 4.5 acetate buffer at about 37° C. at a methazolamide concentration of about 50 mg of methazolamide/900 ml of buffer.

Ibuprofen, U.S. Pat. Nos. 3,228,831 and 3,385,886, is a non-steroidal anti-inflammatory which is useful for the treatment of rheumatoid arthritis, osteoarthritis, mild to moderate pain, and primary dysmenorrhea. It is presently available in many commercial forms (PDR, 43rd Ed.). It is typically administered in dosages of about 1200 mg to about 3200 mg daily in dosages of from about 200 mg to about 800 mg every four to six hours depending on the disease or the symptom being treated for a normal adult human being. Oral dosage units typically comprise from about 200 mg to about 800 mg of ibuprofen.

Preferably, the unit dosage forms of the present invention will release not more than about 60 percent of the ibuprofen from the active spherical granules in about 1 hour and not less than about 90 percent of the ibuprofen from the active spherical granules in about 8 hours when suspended in pH 7.2 phosphate buffer at about 37° C. at an ibuprofen concentration of about 800 mg of ibuprofen/900 ml of buffer.

Disopyramide phosphate is an antiarrhythmic medicament useful for the suppression of and the prevention of recurrence of various cardiac arrhythmias including unifocal premature ventricular contractions, premature ventricular contractions of multifocal origin, paired premature ventricular contractions, and episodes of ventricular tachycardia. It is commercially available in many forms (PDR, 43rd Ed.). It is typically administered in dosages of about 600 mg/daily in dosages from about 100 mg to about 300 mg every six to twelve hours for a normal adult human being. Oral unit dosages typically comprise from about 100 mg to about 300 mg of disopyramide phosphate.

Preferably, the unit dosage forms of the present invention will release disopyramide phosphate from the active granules in the following manner when suspended in pH 2.5 phosphate buffer at about 37° C. at a disopyramide phosphate concentration of from about 100 mg to about 300 mg disopyramide phosphate/900 ml of buffer:

| Time (Hours) | Approximate Drug Released |
| --- | --- |
| 1 | 5-25% |
| 2 | 17-43% |
| 5 | 50-80% |
| 12 | not less than 85% |

Tetracycline compounds are widely used in therapy for their antimicrobial effect. Although broadly applicable to tetracycline compounds in general, it is preferred for purposes of this invention to use members of the tetracycline family comprising substituted 7- and/or 9-amino tetracycline which may be represented by the following general formula:

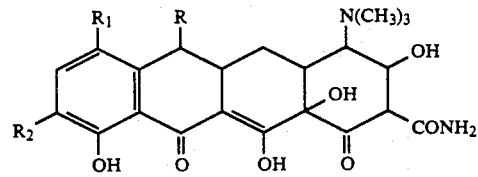

where R is hydrogen or methyl and $R_1$ and $R_2$ are hydrogen, mono(lower alkyl)amino or di(lower alkyl)amino with the proviso that $R_1$ and $R_2$ cannot both be hydrogen. Typical compounds represented by the above general formula are, for example,
7-methylamino-6-deoxy-6-demethyltetracycline,
7-ethylamino-6-deoxy-6-demethyltetracycline,
7-isopropylamino-6-deoxy-6-demethyltetracycline, 9-methylamino-6-deoxy-6-demethyltetracycline,
9-ethylamino-6-deoxy-6-demethyltetracycline,
9-isopropylamino-6-deoxy-6-demethyltetracycline,
7,9-di(ethylamino)-6-deoxy-6-demethyltetracycline,
7-dimethylamino-6-deoxy-6-demethyltetracycline,
9-dimethylamino-6-deoxy-6-demethyltetracycline,
7-methylamino-6-deoxytetracyline,
9-ethylamino-6-deoxytetracyline,
7,9-di(methylamino)-6-deoxytetracycline,
7-diethylamino-6-deoxytetracyline,
9-diethylamino-6-deoxytetracyline,
7,9-di(methylethylamino)-6-deoxytetracycline,
7-methylamino-9-ethylamino-6-deoxytetracycline, and
9-methylamino-5-hydroxy-6-deoxytetracycline.

Preferred members of this family comprise tetracycline compounds selected from
(a) 7-dimethylamino-6-deoxy-6-demethyltetracycline;
(b) 7-methylamino-6-deoxy-6-dimethyltetracycline;
(c) 9-methylamino-6-deoxy-6-demethyltetracycline;
(d) 7-ethylamino-6-deoxy-6-demethyl-tetracycline;
(e) 7-isopropylamino-6-deoxy-6-demethyltetracycline;
(f) a non-toxic acid addition salt of (a)–(e), inclusive or
(g) a mixture of any of the foregoing.

Special mention is made of the tetracycline compound 7-dimethylamino-6-deoxy-6-demethyltetracycline and its non-toxic acid addition salts, e.g., hydrochloric, sulfonic, trichloroacetic acid salts, and the like, especially preferably the hydrochloric acid addition salts. The last named compound is also known as minocycline hydrochloride. These compounds and methods for their preparation are disclosed in commonly assigned Boothe et al, U.S. Pat. No. 3,148,212, and Pesti et al, U.S. Pat. No. 3,226,436. Typically, tetracycline hydrochloride is administered orally in a daily dosage of about one to about two grams divided into two to four equal doses in a normal adult human being. It is commercially available in many forms including the tradename Achromycin® from Lederle Laboratories (PDR, 43rd Ed.). Oral dosage units typically comprise from about 25 mg to about 200 mg of tetracycline compound.

Preferably, the unit dosage forms of the present invention will release not more than about 80 percent of the tetracycline compound from the active spherical granules in about 1 hour, and not less than about 90 percent of the tetracycline compound from the active spherical granules in about 12 hours when suspended in deionized water at about 37° C. at a tetracycline compound concentration of about 50 mg to about 100 mg of tetracycline compound/900 ml of water.

Minocycline hydrochloride for oral administration is a semi-synthetic derivative of tetracycline demonstrating various bacteriostatic properties. It is commercially available under the tradename Minocin® from Lederle Laboratories (PDR, 43rd Ed.). It is typically administered in dosages of about 200 mg initially followed by 100 mg every twelve hours or 200 mg initially followed by 50 mg every six hours in a normal adult human being. Oral dosage units typically comprise from about 50 mg to about 100 mg of minocycline hydrochloride.

Preferaby, the unit dosage forms of the present invention will release not more than about 80 percent of the minocycline hydrochloride from the active spherical granules in about 1 hour and not less than about 90 percent of the minocycline hydrochloride from the active spherical granules in about 12 hours when suspended in deionized water at about 37° C. at a minocycline hydrochloride concentration of about 50 mg to about 200 mg of minocycline compound/900 ml of water.

The normally solid diluent adapted to form a diffusable matrix in either the active spherical granules (A) or in the compressible spherical granules (B) or both preferably comprises microcrystalline cellulose. Suitable forms of microcrystalline cellulose are, for example, the materials sold as Avicel®-PH-101 and Avicel®-PH-105 (available from FMC Corporation, American Viscose Division, Avicel Sales, Marcus Hook, Penna., U.S.A.). The crystalline structure of microcrystalline cellulose is relaxed when combined with excessive or large amounts of water, i.e., greater than about 30 percent by weight of microcrystalline cellulose and water combined, preferably greater than about 50 percent, and most preferably about 75 percent, losing most or all disintegration properties it possessed and forming a diffusable matrix. The normally solid diluent adapted to form a diffusable matrix for use in (A) and/or (B) can also comprise a mixture of microcrystalline cellulose and sodium carboxymethyl cellulose such as the material sold as Avicel® RC-581 by FMC Corporation. The choice of normally solid diluent adapted to form a diffusable matrix in (A) and/or (B) can be manipulated to achieve the desired release rate of the active medicament.

Release rates can also be controlled by the proper selection of excipients in the active spherical granules and in the compressible spherical granules. Such excipients include lactose, other mono- or disaccharides, microcrystalline cellulose, polyvinylpyrrolidone, hydroxypropylmethyl cellulose, microcrystalline cellulose and lactose, microcrystalline cellulose and sodium carboxymethyl cellulose, mixtures of any of the foregoing and the like as well as others with which those skilled in this art will be familiar, most of which are listed in standard references, for example, Remington's Pharmaceutical Sciences, 1985, 17th Edition, Philadelphia College of Pharmacy and Science, Chapter 68, Pharmaceutical Necessities, pages 1278–1320.

The compressible spherical granules of the present invention comprise at least one mono- or di-saccharide; and optionally a pharmaceutically acceptable normally solid diluent and disintegrant as described above, at least one active medicament as described above or a combination of normally solid diluent and disintegrant and active medicament.

The mono- or di-saccharide of the compressible spherical granules preferably comprises lactose. When the compressible spherical granules comprise only at least one mono- or di-saccharide, they may comprise non-pareil seeds. Such seeds are generally about 0.1 to about 2.0 mm in size and typically are about 1.0 millimeter in size. They can comprise, for example, a blend of sugar and starch.

The non-pareil seeds can also be coated with an effective amount of at least one active medicament which may be the same as or different than that found in the active spherical granules.

The active spherical granules of the present invention preferably have an average diameter in the range of from about 0.1 to about 2.5 millimeters. The compressible spherical granules preferably have an average diameter of the same range, i.e. from about 0.1 to about 2.5 millimeters, independent of the average diameter of the active spherical granules. Most preferably, the active spherical granules and the compressible spherical granules independently have an average diameter in the range of from about 0.8 to about 1.2 millimeters.

In a preferred feature of the present invention, either the active spherical granules, the compressible spherical granules, the tablet unit dosage form, any optional nonpareil seeds, or any combination of the foregoing may include a layer or film of a polymer coating which is substantially uniform. Most preferably, this layer or film will comprise a top layer of the same or a different polymer over an intermediate polymer layer.

The film forming polymer, if used, can vary widely in type and amount which correlates to film thickness. This type of polymer should be selected in accordance with the active medicament incorporated into the oral dosage unit form. For example, with respect to tetracycline compounds, it is important that any film forming polymer either be somewhat erodible in gastric juice and/or used in a layer or layers to permit the release of a minor proportion of the tetracycline compound in the stomach because tetracycline compounds typically cause CNS and gastrointestinal side effects including lightheadedness, dizziness, vertigo, nausea, vomitting and diarrhea.

Although from about 1 to less than about 25 weight percent of film content based on the weight of the film coated spheres or tablets is suitable for most readily gastric juice erodible polymers, it is preferred to use about 1 to about 5 percent of any film.

Illustrative but not limiting film forming polymers are cellulose and acrylic acid based polymers. Particularly to be mentioned are methyl cellulose, ethyl cellulose, hydroxyethyl cellulose, hydroxypropyl cellulose, hydroxypropyl methyl cellulose, hydroxypropyl methyl cellulose phthalate, cellulose acetate phthalate, hydroxypropyl methylcellulose succinate, polymers and copolymers of (meth)acrylic acid and (meth)acrylic acid methyl ester, and mixtures of any of the foregoing. The coatings can include conventional additives, such as plasticizers, pigments, colorants, etc. The plasticizers can include mineral oil, high boiling esters, vegetable oils and the like. Commercial coating compositions found to be useful include Eudragit® a product of Rohm Pharma, Weiterstadt, Germany and Surelease®, a product of Colorcon, Inc., West Point, Penna. The former comprises an anionic polymerizate of methacrylic acid and methyl methacrylate. The latter comprises an aqueous dispersion of ethyl cellulose, dibutyl sebacate, oleic acid, fumed silca, and ammonium hydroxide.

Preferred as coating materials are ethylcellulose and hydroxypropyl methylcellulose, and the commercial coatings tabulated herein.

A suitable form of ethylcellulose is one having a viscosity in the range of 5 to 100 cps at 20° C. (U.S. National Formulary XIII)(content of ethoxy groups 44 to 51 percent by weight), and more particularly a viscosity of 50 cps at 20° C. (content of ethoxy groups 48 to 49 percent by weight). A suitable form of hydroxypropyl methylcellulose is one having a viscosity in the range 3 to 100 cps at 20° C., (U.S. National Formulary XIII), and more particularly a viscosity of 6 cps at 20° C.

The spherical granules or tablets can, if desired, be coated with an aqueous or organic solvent solution of the desired film forming polymer, using fluid bed technology or pan-coating, and the like, but preferably fluid beds are used.

For best results, if a film coating is used, a 1 percent weight gain level precoat and overcoat of hydroxypropyl methylcellulose are preferred in addition to the standard coating when using aqueous formulations.

Several formulations comprising polymers suitable for use as film coatings with certain embodiments of tetracycline compounds are shown in Tables I, II, III and IV.

TABLE I

COATING FORMULATIONS FOR MINOCYCLINE HYDROCHLORIDE ACTIVE SPHERICAL GRANULES

| Ingredients | Formulation Number (% W/W) | | | | | |
|---|---|---|---|---|---|---|
| | 1* | 2 | 3** | 4** | 5*** | 6* |
| Hydroxypropyl methylcellulose phthalate (HPMCP) | 75 | 67.5 | 60 | 56.25 | 52.5 | 37.5 |
| Hydroxypropyl methylcellulose (HPMC) | 0 | 7.5 | 15 | 18.75 | 22.5 | 37.5 |
| Mineral Oil | 15 | 15 | 15 | 15 | 15 | 15 |
| Opaspray K-1-2562**** | 10 | 10 | 10 | 10 | 10 | 10 |

*Formulations No. 1, 2 and 6 were applied at 4 percent weight gain level with organic solvents such as methylene chloride or methanol.
**Formulations No. 3 and 4 were applied at 2 percent and 4 percent weight gain level.
***Formulation No. 5 was applied at 4 percent and 8 percent weight gain level.
****Colorcon Inc., orange-colored dye composition.

TABLE II

PRECOAT/OVERCOAT FORMULATION FOR MINOCYCLINE HYDROCHLORIDE ACTIVE SPHERICAL GRANULES

| INGREDIENT | % (W/W) |
|---|---|
| Hydroxypropyl methylcellulose | 71 |
| Sodium lauryl sulfate | 4 |
| Mineral Oil | 25 |
| Water (added at 9 times the total weight of the above solids) | |

This solution is applied at a 1 percent weight gain level, as a precoat and again as an overcoat on minocycline hydrochloride active spherical granules when applying aqueous coatings.

TABLE III

COATING FORMULATION FOR MINOCYCLINE HYDROCHLORIDE ACTIVE SPHERICAL GRANULES

| INGREDIENT | % (W/W) |
|---|---|
| Surelease ® | 60 |
| Water | 40 |

This solution is applied at 2, 3 and 5 percent weight gain levels to minocycline hydrochloride active spherical granules.

TABLE IV

COATING FORMULATION FOR MINOCYCLINE HYDROCHLORIDE ACTIVE SPHERICAL GRANULES

| INGREDIENT | % (W/W) |
|---|---|
| Surelease ® | 77 |
| Eudragit ® L30D* | 20 |
| Hydroxypropyl methylcellulose | 3 |
| Water (added at 6 times the total weight of the above solids) | |

*Product of Rohm Pharma, Weiterstadt, Germany

This solution is applied at 2 to 10 percent weight gain levels.

The tablet unit dosage form of the present invention can be made divisible by scoring or the like.

The amounts of components (A)(i), (A)(ii) and (A)(iii) which comprise the active spherical granules (A) can vary broadly but will usually be in the range of from about 10 to about 90 parts by weight of (A)(i), from about 90 to about 10 parts by weight of (A)(ii), and from zero to about 75 parts by weight of (A)(iii) based upon 100 parts by weight of active spherical granules (A). Preferably, the active spherical granules comprise either from about 10 to about 75 parts by weight of (A)(i), and from about 90 to about 25 parts by weight of (A)(ii) based upon 100 parts by weight of (A) or from about 10 to about 80 parts by weight of (A)(i), from about 75 to about 10 parts by weight of (A)(ii), and from about 10 to about 75 parts by weight of (A)(iii) based upon 100 parts by weight of (A). Most preferably, (A)(i) comprises about 50 parts by weight by weight and (A)(ii) comprises about 50 parts by weight based upon 100 parts by weight of (A) or from about 10 to about 50 parts by weight of (A)(i), from about 25 to about 65 parts by weight of (A)(ii), and from about 10 to about 50 parts by weight of (A)(iii) based upon 100 parts by weight of (A). Special mention is made where (A) comprises about 25 parts by weight of (A)(i), from about 25 to about 65 parts by weight of (A)(ii) and from about 10 to about 50 parts by weight of (A)(iii) based upon 100 parts by weight of (A).

The amounts of (B)(i), (B)(ii),(B)(iii), (B)(iv) and (B)(v) may also vary broadly, but compressible spherical granules (B) will usually comprise from about 10 to about 100 parts by weight of (B)(i), from zero to about 90 parts by weight of (B)(ii), and from zero to about 90 parts of (B)(iv) based upon 100 parts by weight of compressible spherical granules (B). Preferably, (B)(i) comprises from about 25 to about 90 parts by weight and (B)(ii) comprises from about 75 to about 10 parts by weight based upon 100 parts by weight of (B) or (B)(i) comprises from about 50 to about 90 parts by weight and (B)(ii) comprises from about 10 to about 50 parts by weight based upon 100 parts by weight of (B). Most preferably, (B)(i) comprises about 75 parts by weight and (B)(ii) comprises about 25 parts by weight based upon 100 parts by weight of (B).

Additionally, the amounts of (A) and (B) will vary broadly, but will generally be in the range of from about 10 to about 90 parts by weight of (A) and from 90 to about 10 parts by weight of (B) based upon 100 parts by weight of (A) and (B) combined. Preferably, (A) comprises about 50 parts by weight and (B) comprises about 50 parts by weight based upon 100 parts by weight of (A) and (B) combined.

The therapeutically effective amount of active spherical granules can comprise a mixture of two or more independently therapeutically effective amounts of two or more active spherical granules formed into a single tablet along with one or more types of compressible spherical granules.

Figure 5:
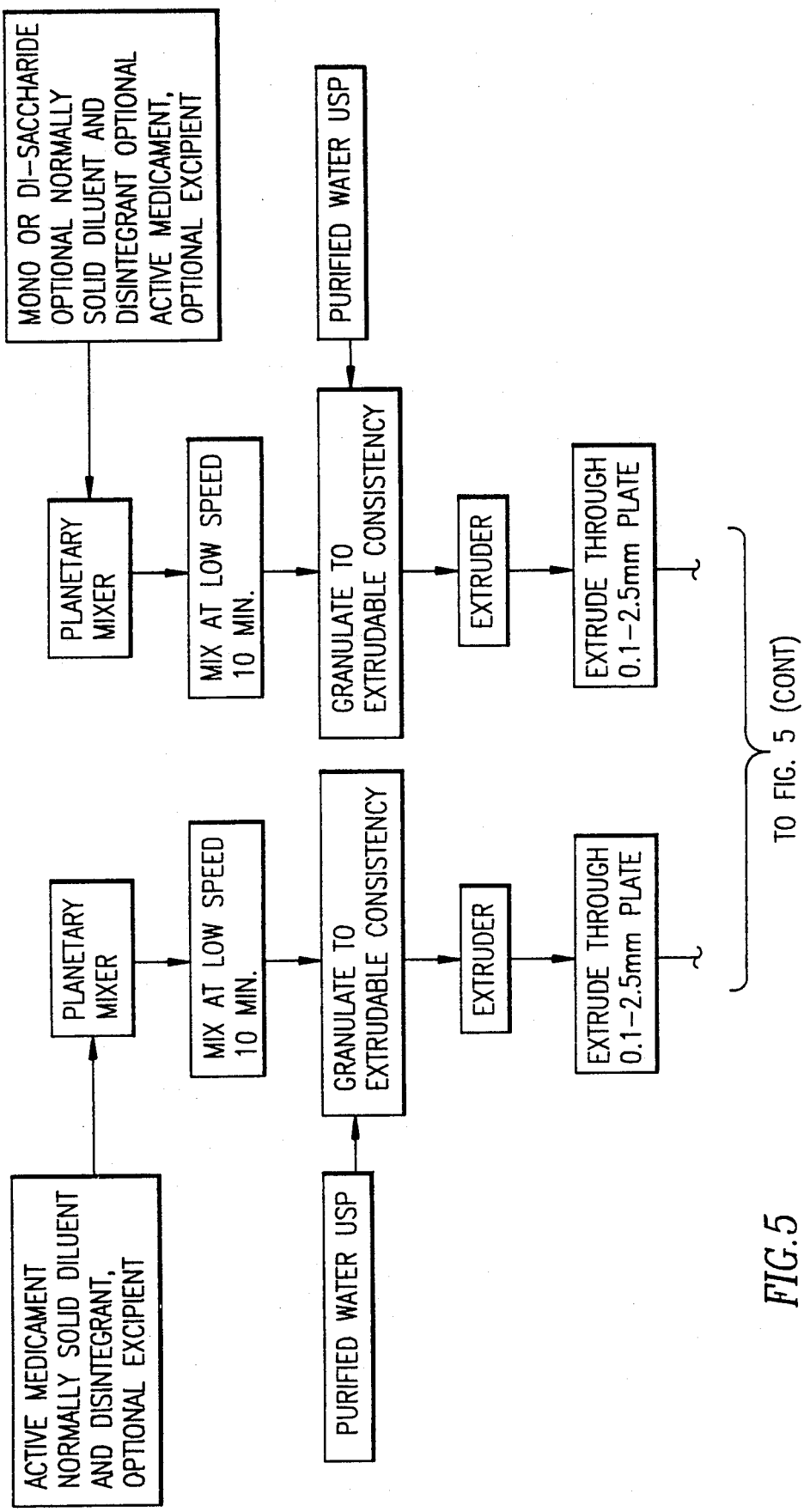
FIG. 5 is a graphic illustration of a method for the production of tablets according to the present invention.
Figure 5:
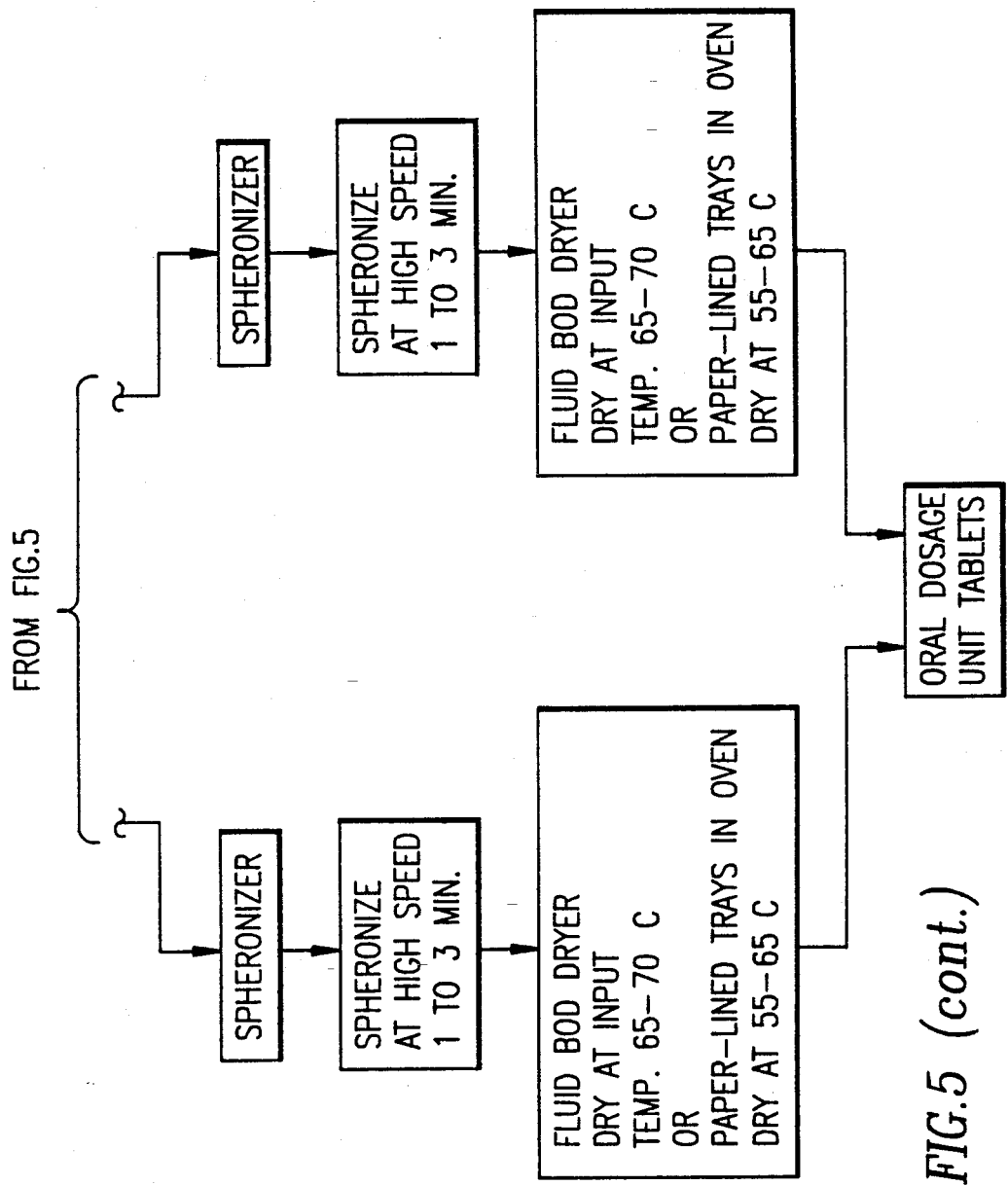

The oral dosage unit tablets of the invention can be made using conventional pharmaceutical production equipment. The hardness of the tablets does not affect the controlled release properties of the active spherical granules. FIG. 5 illustrates the typical steps in the preparation of the oral unit dosage forms of the present invention. Firstly, in step (a), an effective amount of at least one active medicament (a)(i), a pharmaceutically acceptable normally solid diluent adaptable to form a diffusable matrix for said at least one active medicament (a)(i), (a)(ii), and optionally, at least one pharmaceutically acceptable excipient which may be the same as or different than (a)(ii) is blended. Independently, in step (b), at least one mono- or di-saccharide (b)(i); optionally, a pharmaceutically acceptable normally solid diluent adaptable to form a diffusable matrix which may be the same as or different than (a)(ii), (b)(ii); optionally, an effective amount of at least one active medicament which may be the same as or different than (a)(i), (b)(iii); optionally, at least one pharmaceutically acceptable excipient other than a mono- or di-saccharide which may be the same as or different than either (a)(i) or (a)(ii), (b)(iv); or optionally a combination of any of (b)(ii), (b)(iii) and (b)(iv), (b)(v), is blended in a mixer, e.g. a Hobart mixer. The resultant blends of steps (a) and (b) are independently granulated with a liquid medium, e.g. an aqueous solution or an organic solvent and preferably water, until the proper consistency, e.g. greater than about 30 percent water, preferably greater than about 50 percent and most preferably 75 percent water, for extrusion is realized. The resultant granulated masses are then independently extruded through a suitably sized, e.g. 1.0 mm, perforated plate and spheronized at high speed for a time sufficient to form spherical granules, e.g. one to three minutes. Active spherical granules (A) are formed from the spheronization of the extrudate derived from step (a) and compressible spherical granules (B) are formed from the spheronization of the extrudate derived from step (b). The wet spherical granules are then dried in conventional equipment at suitable temperatures, e.g. such as tray driers at 55° to 65° C., or a conventional fluidized bed dryer system at 65° to 70° C., to a low moisture level, e.g. about 2 to about 6 percent. The components may then, optionally, be coated as explained above. The average compressive yield of components (B) should be less than the average compressive yield of components (A). A therapeutically effective number of active spherical granules (A) and a number of compressible spherical granules (B) are then formed into a tablet oral unit dosage form by conventional means known to one of ordinary skill in the pharmaceutical arts, e.g. compression or pressing. The tablet may then, optionally, be coated as explained above.

The oral dosage unit forms described above may release the active medicament(s) into the blood stream of a warm-blooded mammal after ingestion.

The oral dosage unit forms of the present invention may also optionally include lubricants, additional disintegrants which are either the same as or different than those present in (A)(ii) or (B)(ii), plasticizers, colorants, pigments, flavorings, additional active medicaments which are the same as or different than those present in either (A)(i) or (B)(iii), or a combination of any of the foregoing.

DESCRIPTION OF THE PREFERRED EMBODIMENTS

The following examples illustrate the invention without limitation. All parts are given by weight unless otherwise indicated.

EXAMPLE 1

A blend is prepared by mixing 10 parts of active medicament, methazolamide (Neptazane ®, Lederle Laboratories, Inc.), and 90 parts of normally solid diluent adaptable to form a diffusable matrix for the active medicament, microcrystalline cellulose (Avicel ® PH-101 - FMC Corp.), in a planetary mixer for 10 minutes at low speed. The blend is then granulated to an extrudable consistency with the addition of water, and the resultant granulate is extruded through a 1.0 mm plate. The resultant extrudate is spheronized at high speed for one to three minutes. The resultant spherical granules are dried in a fluid bed dryer at 65° C.-70° C. until the moisture content is about 3 to 5 percent to form active spherical granules. Compression properties are measured in an Instron machine and are summarized in Table V.

A dissolution profile of the active medicament in the active spherical granules is determined by U.S.P. XXI test methods using a dissolution medium with a pH of 4.5 and an acetate buffer and stirring with paddles. The results appear in FIG. 14 in graph form.

EXAMPLE 2

The procedure of Example 1 is followed substituting a blend of 25 parts of methazolamide (Neptazane ®), and 75 parts of microcrystalline cellulose (Avicel ® PH-101). Properties are summarized in Table V.

EXAMPLE 3

The procedure of Example 1 is followed substituting a blend of 50 parts of methazolamide (Neptazane ®) and 50 parts of microcrystalline cellulose (Avicel ® PH-101). Properties are summarized in Table V.

EXAMPLE 4

The procedure of Example 1 is followed substituting a blend of 75 parts of methazolamide (Neptazane ® ) and 25 parts of microcrystalline cellulose (Avicel. PH-101). Properties are summarized in Table V.

EXAMPLE 5

The procedure of Example 1 is followed substituting a blend of 25 parts of methazolamide (Neptazane ®), 65 parts of microcrystalline cellulose (Avicel ® PH-101) and 10 parts of excipient, lactose. Properties are summarized in Table V.

EXAMPLE 6

The procedure of Example 1 is followed substituting a blend of 25 parts of methazolamide (Neptazane ®), 50 parts of microcrystalline cellulose (Avicel ® PH-101) and 25 parts of lactose. Properties are summarized in Table V.

EXAMPLE 7

The procedure of Example 1 is followed substituting a blend of 25 parts of methazolamide (Neptazane ®), 25 parts of microcrystalline cellulose (Avcel ® PH-101), and 50 parts of lactose. Properties are summarized in Table V.

EXAMPLE 8

A blend is prepared by mixing 90 parts of mono- or di-saccharide, lactose, and 10 parts of normally solid diluent adaptable to form a diffusable matrix, microcrystalline cellulose (Avicel ® PH-101) in a planetary mixer for 10 minutes at low speed. The blend is then granulated to an extrudable consistency with the addition of water, and the resultant granulate is extruded through a 1.0 mm plate. The resultant extrudate is spheronized at high speed for one to three minutes. The resultant spherical granules are dried in a fluid bed dryer at 65° C.-70° C. until the moisture content is about 3 to 5 percent to form compressible spherical granules. Compression properties are measured in an Instron machine and are summarized in Table V.

COMPARATIVE EXAMPLE 8A*

The procedure of Example 8 is followed substituting only 100 parts of microcrystalline cellulose for the blend. Properties are summarized in Table V.

EXAMPLE 9

The procedure of Example 8 is followed substituting a blend of 25 parts of lactose and 75 parts of microcrystalline cellulose (Avicel ® PH-101). Properties are summarized in Table V.

EXAMPLE 10

The procedure of Example 8 is followed substituting a blend of 50 parts of lactose and 50 parts of microcrystalline cellulose (Avicel PH-101). Properties are summarized in Table V.

EXAMPLE 11

The procedure of Example 8 is followed substituting a blend of 75 parts of lactose and 25 parts of microcrystalline cellulose (Avicel ® PH-101). Properties are summarized in Table V.

TABLE V

COMPRESSIVE PROPERTIES OF ACTIVE AND COMPRESSIBLE SPHERICAL GRANULES

| | Example | | | | | |
|---|---|---|---|---|---|---|
| | 1 | 2 | 3 | 4 | 5 | 6 |
| Active Medicament[A] | 10 | 25 | 50 | 75 | 25 | 25 |
| Normally Solid Diluent Adaptable to Form a Diffusable Matrix for Active Medicament[B] | 90 | 75 | 50 | 25 | 65 | 50 |
| Normally Solid Diluent Adaptable to Form a Diffusable Matrix[C] | — | — | — | — | — | — |
| Excipient[D] | — | — | — | — | 10 | 25 |
| Mono- or Di-saccharide[E] | — | — | — | — | — | — |
| COMPRESSIVE MODULUS (KG/mm²) | 20.82 ± 5.04 | 22.62 ± 3.88 | 18.19 ± 3.90 | 17.75 ± 2.48 | 22.65 ± 6.42 | 28.39 ± 11.72 |
| PEAK LOAD (KG) | 1.082 ± 0.18 | 0.960 ± 0.15 | 0.769 ± 0.23 | 0.374 ± 0.06 | 0.878 ± 0.16 | 1.061 ± 0.23 |
| | Example | | | | | |
| | 7 | 8 | 8A* | 9 | 10 | 11 |
| Active Medicament[A] | 25 | — | — | — | — | — |
| Normally Solid Diluent Adaptable to Form a Diffusable Matrix for | 25 | — | — | — | — | — |

TABLE V-continued
COMPRESSIVE PROPERTIES OF ACTIVE AND COMPRESSIBLE SPHERICAL GRANULES

| | | | | | | |
|---|---|---|---|---|---|---|
| Active Medicament[B] | | | | | | |
| Normally Solid Diluent Adaptable to Form a Diffusable Matrix[C] | — | 10 | 100 | 75 | 50 | 25 |
| Excipient[D] | 50 | — | — | — | — | — |
| Mono- or Di-saccharide[E] | — | 90 | — | 25 | 50 | 75 |
| COMPRESSIVE MODULUS (KG/mm$^2$) | 19.97 ± 7.28 | 19.69 ± 4.41 | 20.94 ± 4.41 | 22.32 ± 4.23 | 22.86 ± 5.92 | 27.50 ± 9.7 |
| PEAK LOAD (KG) | 0.594 ± 0.12 | 0.563 ± 0.31 | 1.15 ± 0.38 | 1.023 ± 0.33 | 1.046 ± 0.29 | 0.522 ± 0.16 |

[A]methazolamide (Neptazane ®, Lederle Laboratories, Inc.)
[B]microcrystalline cellulose (Avicel ® PH-101, FMC Corp.)
[C]microcrystalline cellulose (Avicel ® PH-101, FMC Corp.)
[D]lactose
[E]lactose

EXAMPLE 12

A blend of 25 parts (0.1 gm) of active spherical granules prepared by the procedure of Example 3 containing 50 mg of active medicament, 74.9 parts (0.2996 gm) of compressible spherical granules prepared by the procedure of Example 9, and 0.1 part (0.0004 gm) of lubricant is compressed into a tablet.

Microscopic examination of the tablet reveals a uniform distribution of substantially unbroken active spherical granules throughout.

Active medicament release rate is determined by U.S.P. XXI test methods in pH 4.5 acetate buffer and compared with a theoretical release rate which was determined from pharmacological data available to those of ordinary skill in the art to provide recommended plasma level concentrations of active medicament when the controlled release tablet is administered only twice daily. The results appear in FIG. 6 in graph form.

Figure 7:
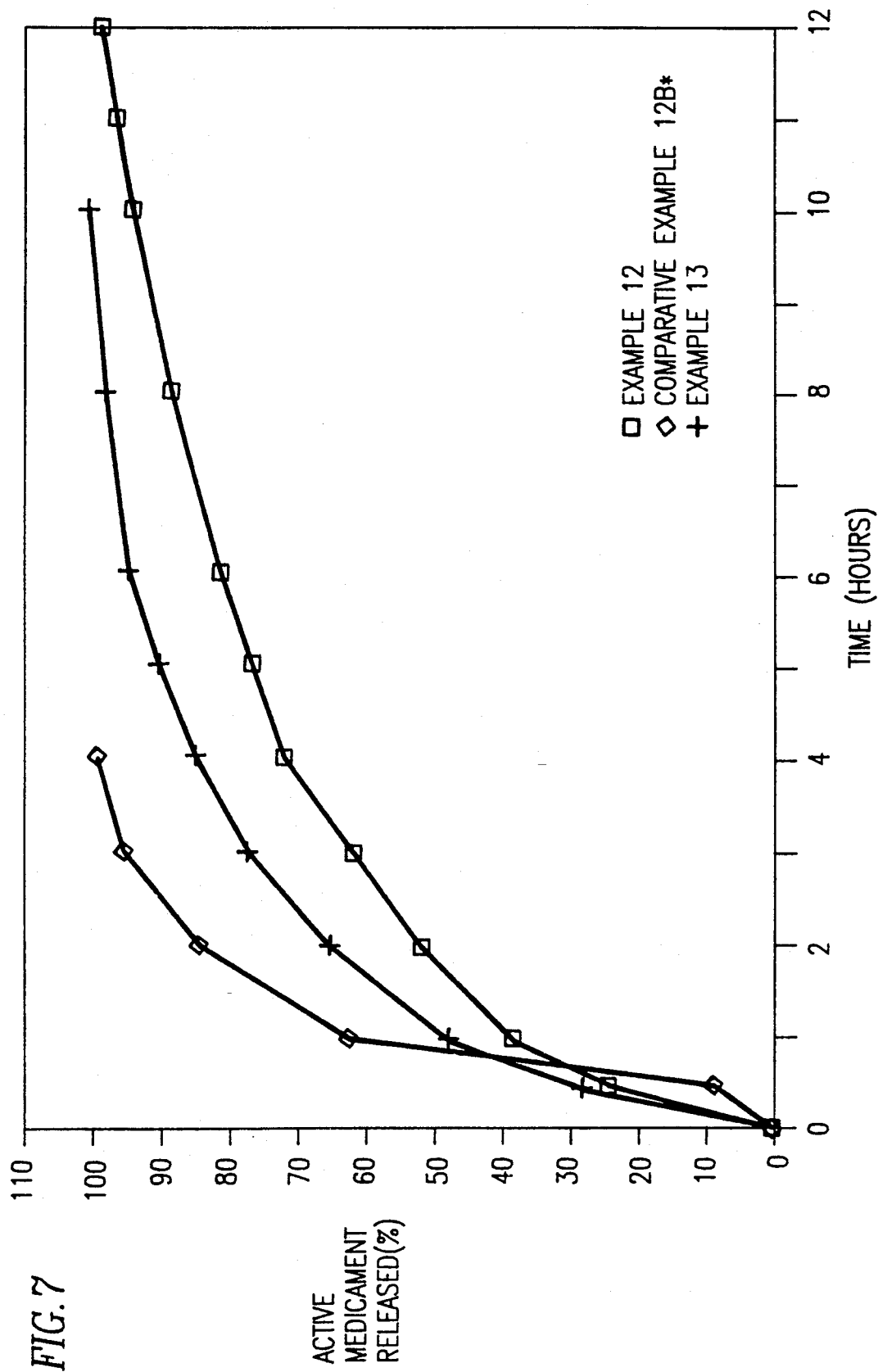
FIG. 7 is a graphic illustration of release rates of Neptazane ® (methazolamide-Lederle Laboratories, Wayne, N.J.) from oral dosage unit forms of the present invention and oral dosage unit forms formulated without compressible spherical granules.

A dissolution profile of the active medicament is determined by U.S.P. XXI test methods using a dissolution medium with a pH of 4.5 and an acetate buffer and stirring with paddles. The result appears in FIG. 7 in graph form.

One tablet is administered daily to each of nine human subjects for a period of four weeks, and plasma concentration levels of active medicament are measured. The results appear in FIG. 8 in graph form.

On day 35 in week 5 of treatment, four of the subjects fast while five eat regularly. Plasma concentration levels of active medicament are measured, and results appear in FIG. 9 in graph form.

Figure 13:
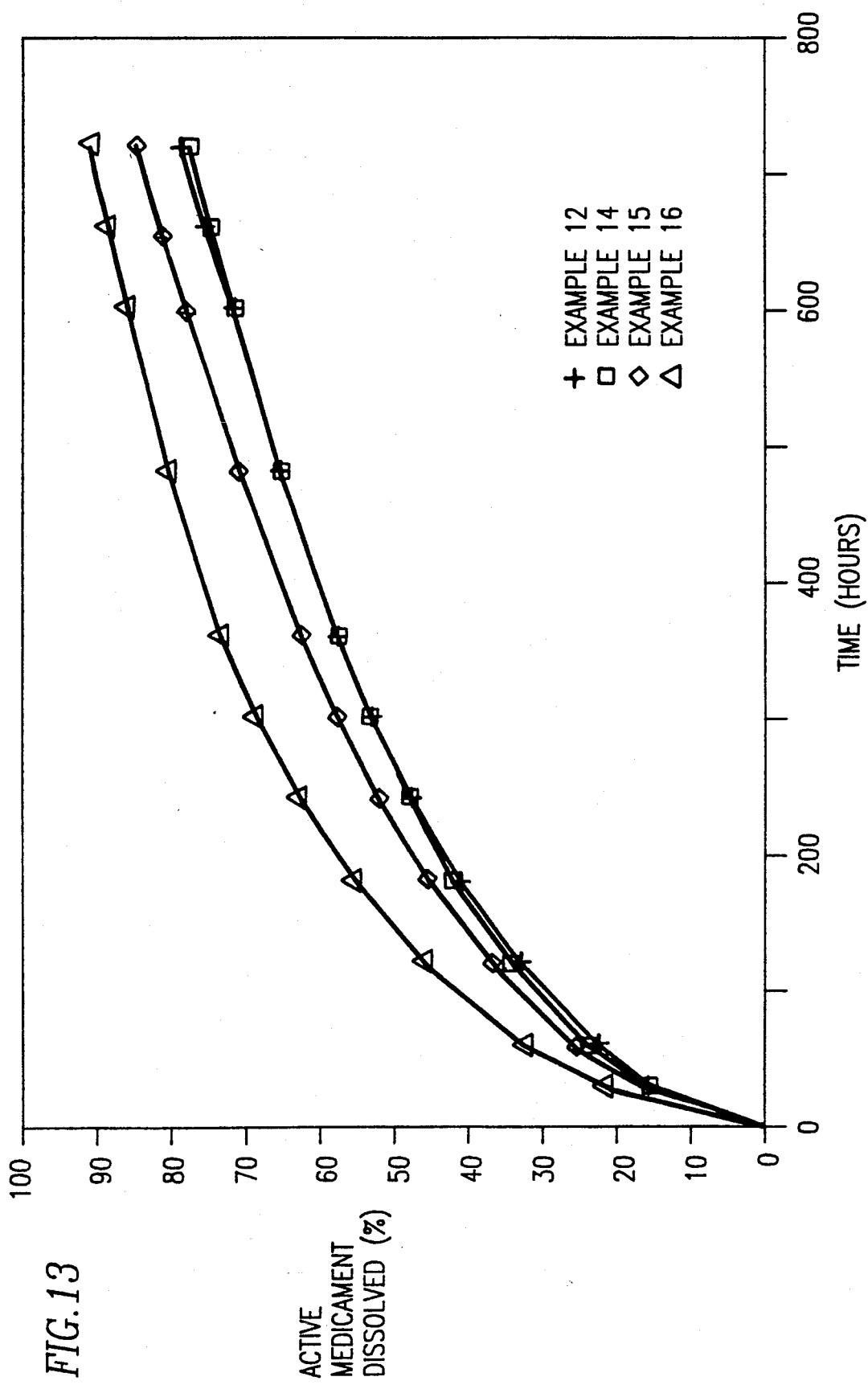
FIG. 13 is a graphic illustration of the effect of spherical granule size on the dissolution rates of oral unit dosage forms according to the present invention.

The effects of sphere size appear in FIG. 13 in graph form.

Stability studies are also conducted under various conditions. The results are summarized in Table VI.

TABLE VI
STABILITY OF NEPTAZANE ® ACTIVE SPHERICAL GRANULE/COMPRESSIBLE SPHERICAL GRANULE TABLETS

| Condition °C./months | Dissolution (% LP)[A] 1 hr/3 hr | Potency (mg)[B] |
|---|---|---|
| 23/0 | 38.0/62.6 | 50.12 |
| 23/3 | 40.6/66.8 | 50.91 |
| 23/6 | 36.3/62.5 | 51.48 |
| 23/9 | 41.2/66.4 | 49.70 |
| 23/12 | 30.4/57.4 | 50.00 |
| 42/1 | ND[D] | 47.91 |
| 42/2 | 46.0/73.6 | 48.45 |
| 42/4 | ND[D] | 49.70 |
| 56/½ | ND[D] | 51.00 |
| 56/1 | ND[D] | 49.75 |
| 56/2 | ND[D] | 51.80 |
| RHHC[C]/1 | 36.8/57.9 | 49.11 |
| RHHC[C]/2 | 34.1/57.6 | 50.12 |
| RHHC[C]/3 | 37.6/61.2 | 52.78 |

[A]Percent label potency; U.S.P. XXI test method; dissolution medium pH 4.5 with acetate buffer; stirred with paddles. Original label potency (LP) 50 mg.
[B]Original potency 50 mg.
[C]Relative humidity chamber - 40° C., 75% relative humidity.
[D]Not Determined.

COMPARATIVE EXAMPLE 12A*

25 mg of active medicament in tablet form not prepared according to the present invention and currently commercially available (methazolamide, Neptazane ®, 25 mg/tablet, Lederle Laboratories) is administered twice daily to each of nine human subjects for a period of four weeks, and plasma concentration levels of the active medicament are measured. The results appear in FIG. 10 in graph form.

COMPARATIVE EXAMPLE 12B*

A blend of 99.9 parts (0.1998 gm) of active spherical granules prepared by the procedure of Example 7, and 0.1 part (0.0004 gm) of lubricant is compressed into a tablet. A dissolution profile of the active medicament is determined by U.S.P. XXI test methods using a dissolution medium with a pH of 4.5 and an acetate buffer and stirring with paddles. The results appear in FIG. 7 in graph form.

One tablet is administered daily to each of nine human subjects for a period of four weeks, and plasma concentration levels of active medicament are measured. The results appear in FIG. 11 in graph form.

EXAMPLE 13

A blend of 50 parts (0.2 gm) of active spherical granules prepared by the procedure of Example 6 containing 50 mg of active medicament, 49.9 parts (0.1996 gm) of compressible spherical granules prepared by the procedure of Example 9, and 0.1 part (0.0004 gm) of lubricant is compressed into a tablet.

Microscopic examination of the tablet reveals a uniform distribution of substantially unbroken active spherical granules throughout.

A dissolution profile of the active medicament is determined by U.S.P. XXI test methods using a dissolution medium with a pH of 4.5 and an acetate buffer and stirring with paddles. The results appear in FIG. 7 in graph form.

One tablet is administered daily to each of nine human subjects for a period of four weeks, and plasma concentration levels of active medicament are measured. The results appear in FIG. 12 in graph form.

Figure 6:
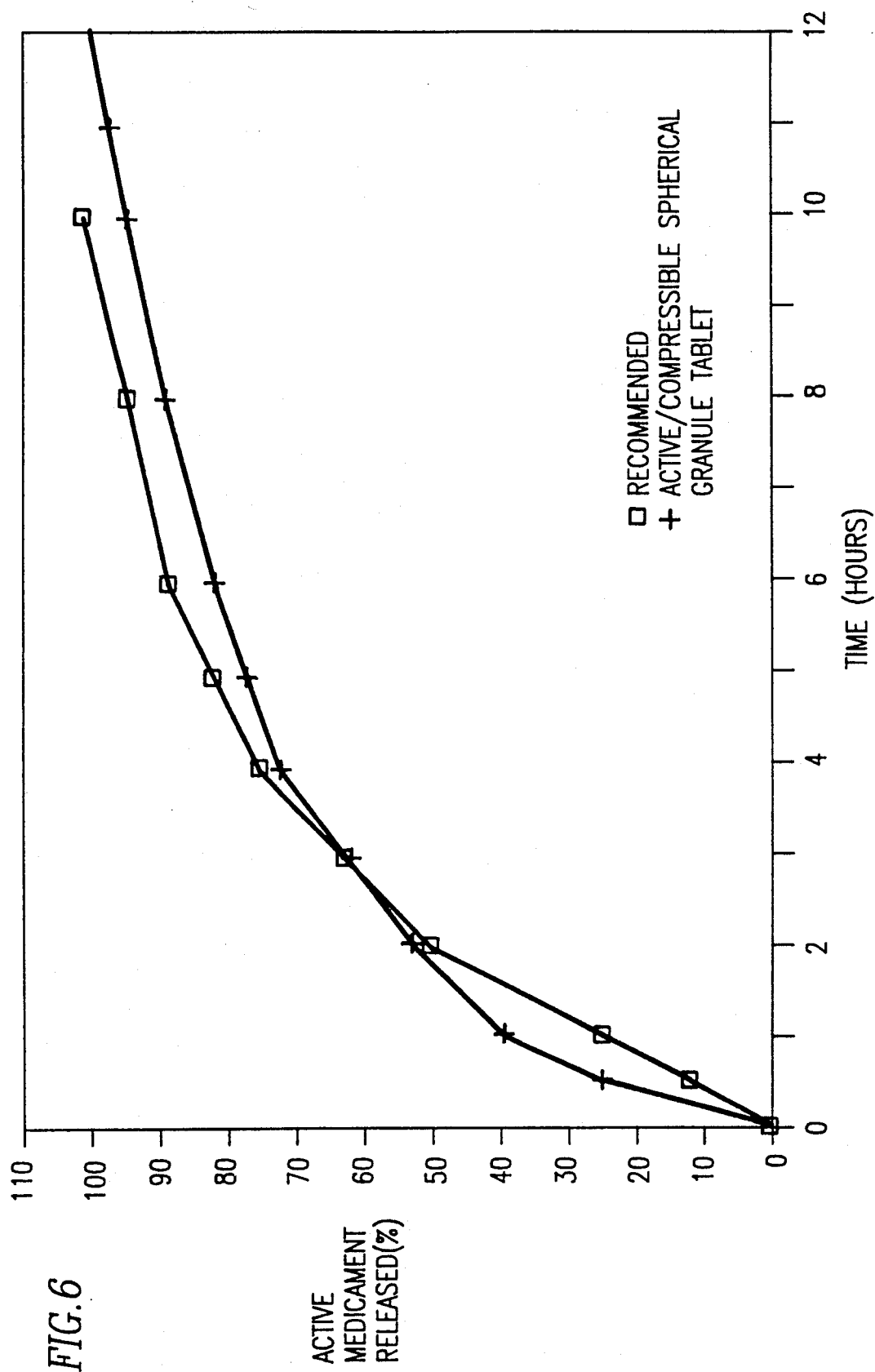
FIG. 6 is a graphic illustration of the release rate of active medicament from a unit dosage form of the present invention in comparison with a desired, theoretically derived release rate for the same active medicament.

Example 12 and FIG. 6 demonstrate that the release rate of active medicament from oral dosage unit tablets of the present invention provide a controlled release of active medicament and will deliver a therapeutically effective amount of active medicament to a subject for at least twelve hours.

Examples 12 (FIG. 8) and 13 (FIG. 12) when compared with Comparative Example 12A* and 12B* demonstrate relatively level prolonged release of active medicament in human subjects from tablets formulated in accordance with the present invention as opposed to the peaked and complete release of active medicament in a relatively short period of time from tablets not formulated according to the present invention.

Figure 8:
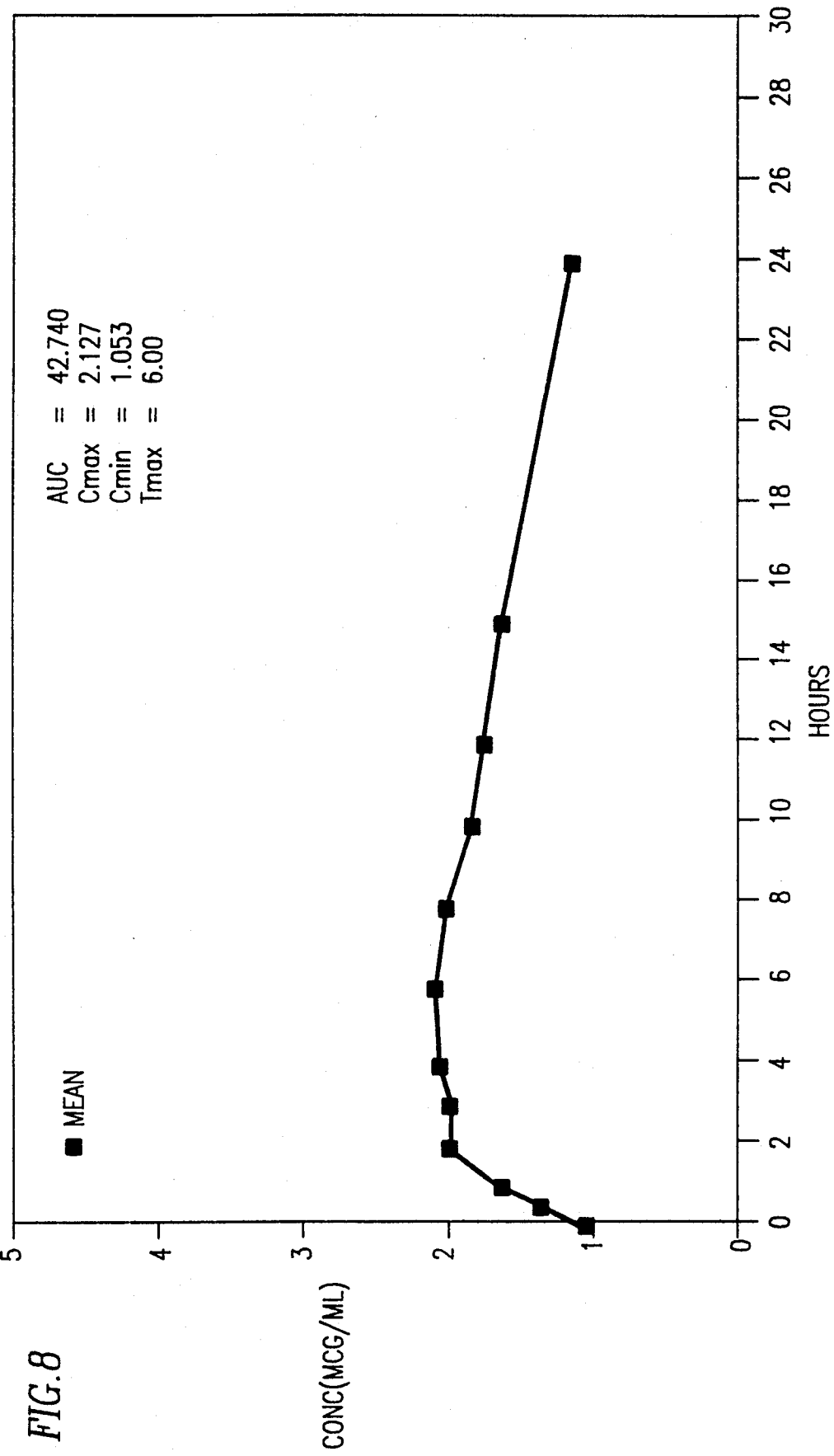
FIG. 8 is a graphic illustration of plasma concentration levels of Neptazane ® administered to human patients in oral unit dosage forms according to the present invention when it is given once a day in a 50 mg strength.
Figure 10:
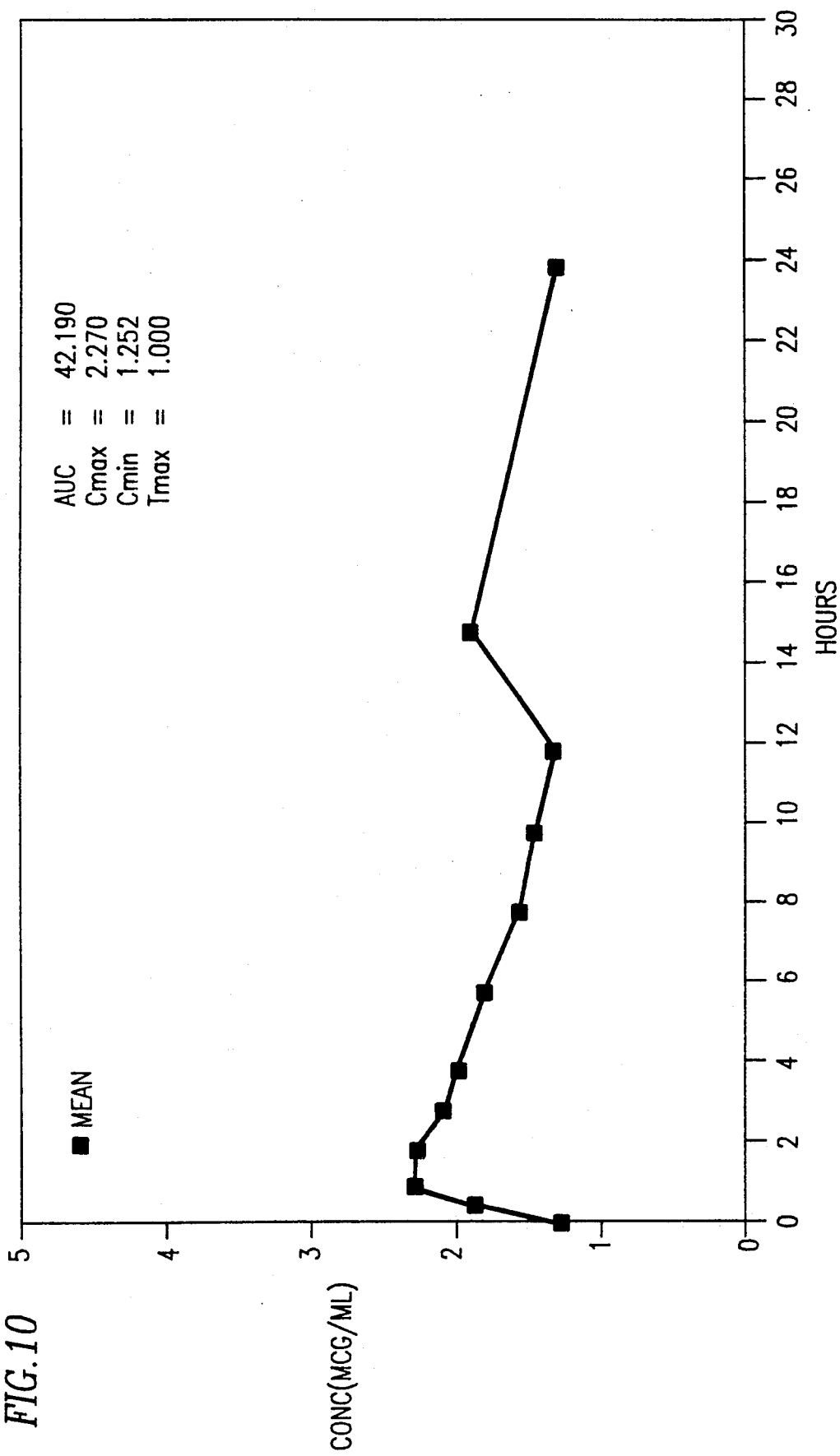
FIG. 10 is a graphic illustration of plasma concentration levels of Neptazane ® administered twice a day to human patients in oral dosage forms comprising 25 mg immediate release tablets presently available from Lederle Laboratories.

The area under the curve (AUC) measurement of FIG. 10 indicates that total active medicament received by a subject treated twice daily with tablets currently available commercially. The AUC values of FIGS. 8 and 12 compare favorably with the total active medicament released from the tablets of FIG. 10 but are the result of only one dosage daily, indicating that less frequent administrations and lower overall dosages of active medicament in oral dosage unit tablets of the present invention provide therapeutically effective plasma level concentrations of active medicament for prolonged periods of time. Maximum (Cmax) and minimum (Cmin) concentrations for FIGS. 8 and 12 also conform closely to those in FIG. 10. The AUC of FIG. 11 is considerably higher than that of FIG. 10 indicating a considerably higher amount of total active medicament released.

Figure 11:
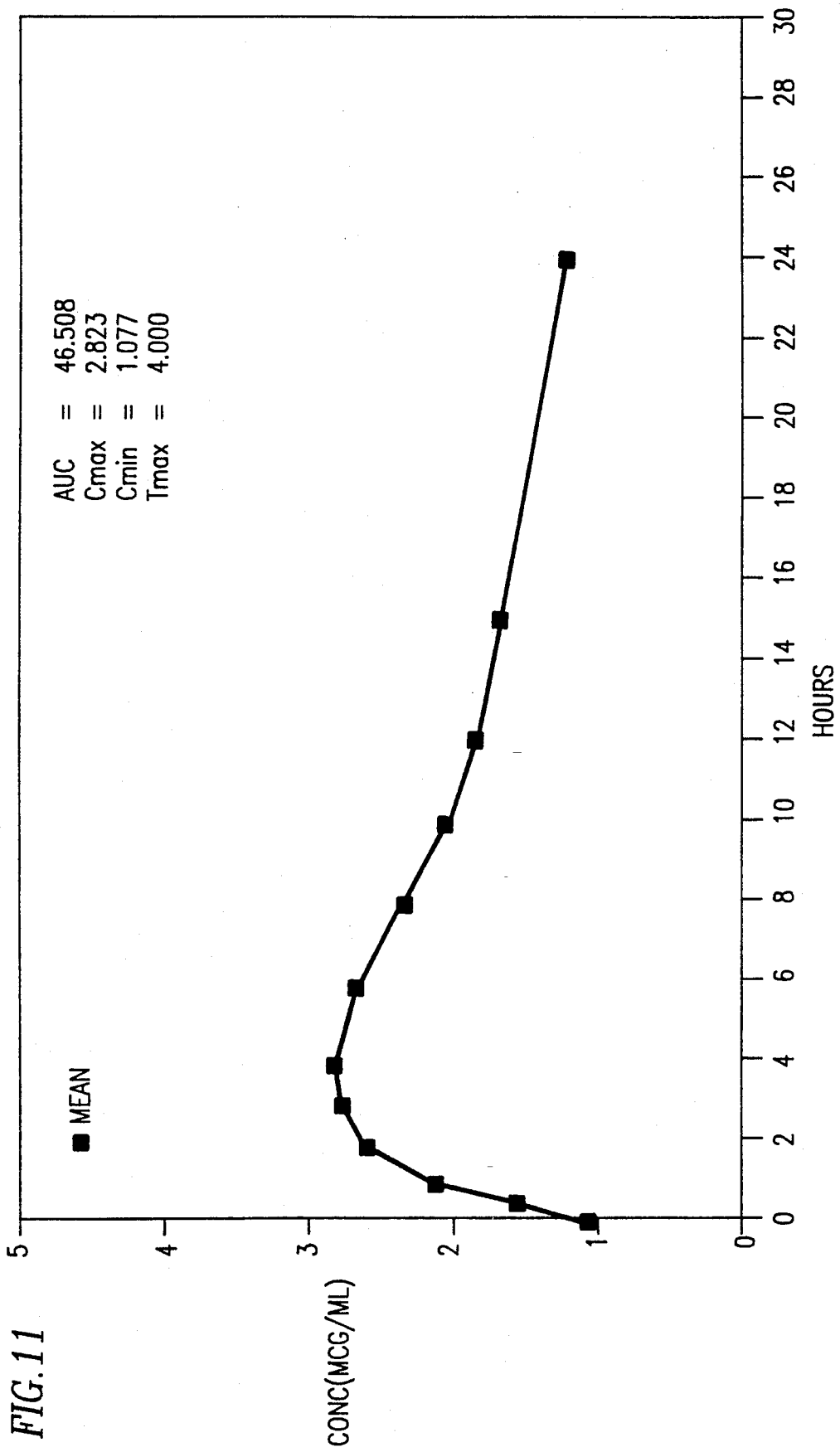
FIG. 11 is a graphic illustration of plasma concentration levels of Neptazane ® administered once a day in a 50 mg strength to human patients in tabletted oral dosage forms comprising active spherical granules without compressible spherical granules.
Figure 12:
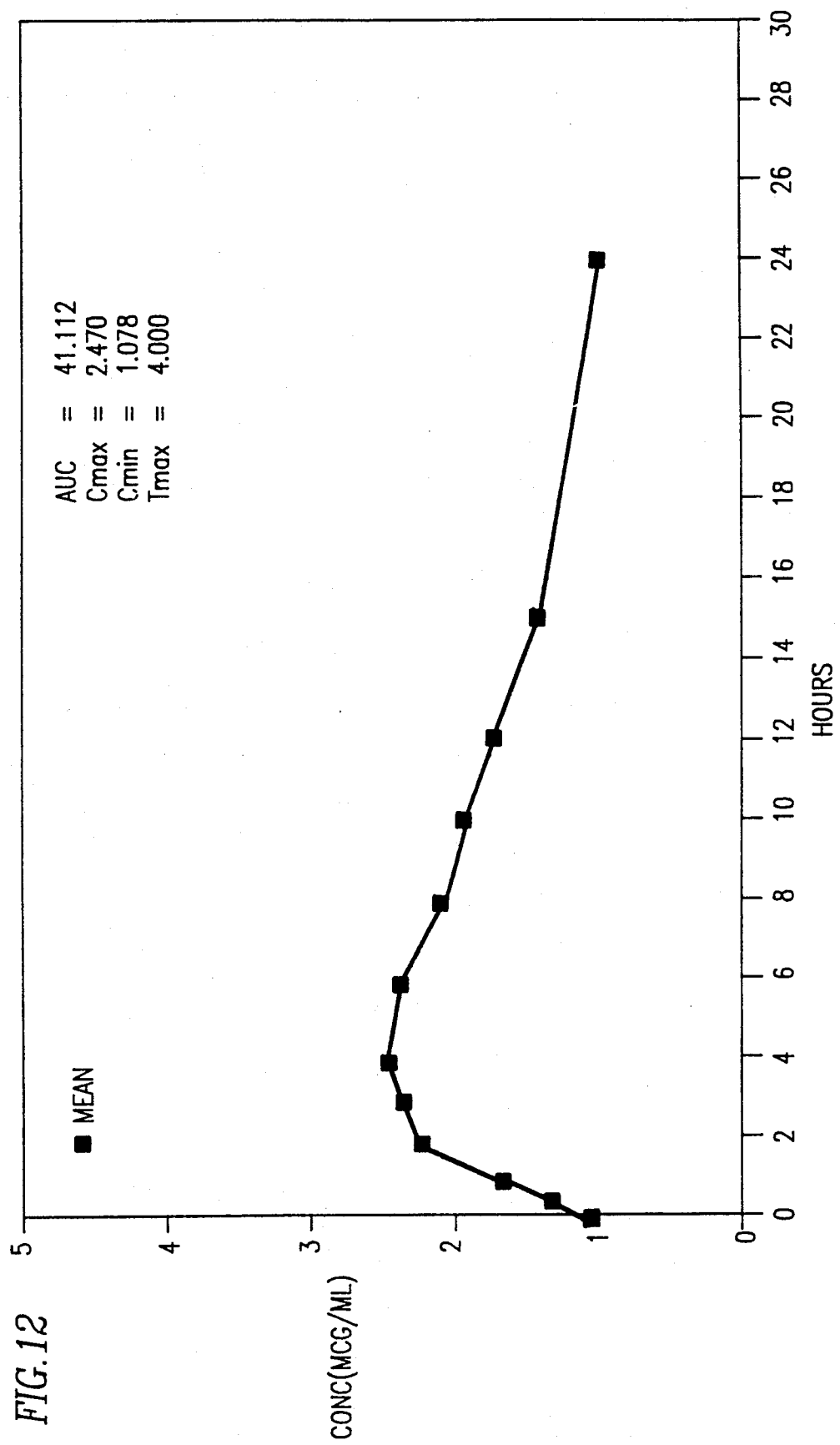
FIG. 12 is a graphic illustration of plasma concentration levels of Neptazane ® administered to human patients once a day in a 50 mg strength oral dosage unit form with a different release profile than the FIG. 8 unit dosage form but prepared in accordance with the present invention.

The high maximum concentration in FIG. 11 indicates a relatively rapid, less controlled release than that of FIGS. 8 and 12. The relative times that maximum concentration are reached show that tablets formulated according to the present invention provide a gradual and even release of medicament.

Figure 9:
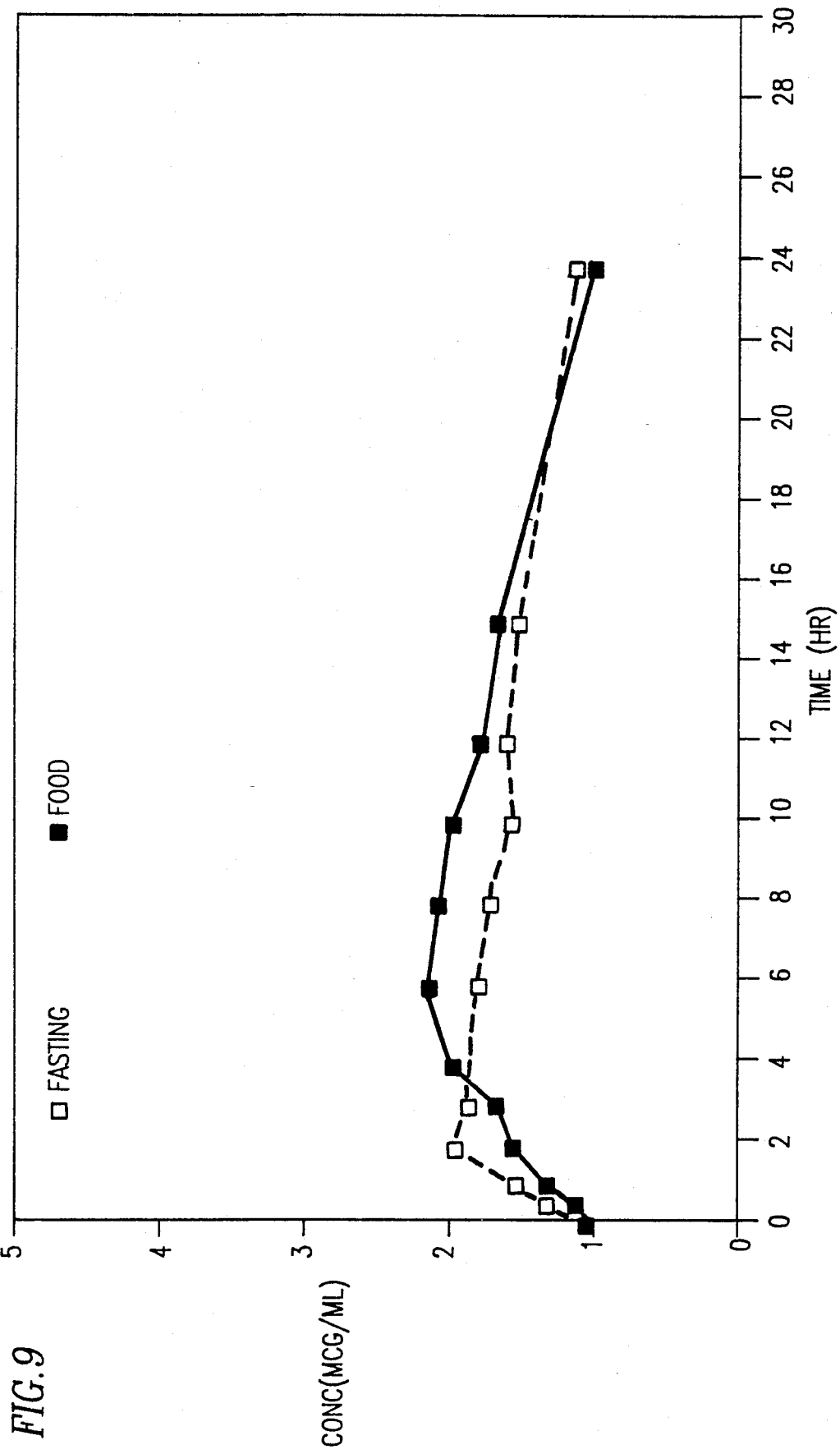
FIG. 9 is a graphic illustration of plasma concentration levels of Neptazane administered once a day in a 50 mg strength to fasting human patients in oral dosage unit forms according to the present invention compared with non-fasting human patients.

FIG. 9 indicates that the controlled release properties of tablets formulated according to the present invention are only minimally affected by fasting.

The results all strongly indicate that the dosage units of the invention will deliver therapeutically effective amounts of active medicament to a subject over a prolonged period of time requiring less frequent administration of the active medicament and lower total dosages of the active medicament.

EXAMPLE 14

A blend is prepared by mixing 50 parts of active medicament, methazolamide (Neptazane ®), and 50 parts of normally solid diluent adaptable to form a diffusable matrix for the active medicament, microcrystalline cellulose (Avicel ® PH-101), in a planetary mixer for 10 minutes at low speed. The blend is then granulated to an extrudable consistency with the addition of 300 parts of water, and the resultant granulate is extruded through a 1.2 to 1.8 mm plate. The resultant extrudate is spheronized at high speed for one to three minutes. The resultant sperical granules are dried in a fluid bed dryer at 65° C.–70° C. until the moisture content is about 3 to 5 percent to form active spherical granules.

A blend is prepared by mixing 75 parts of mono- or di-saccharide, lactose, and 25 parts of normally solid diluent adaptable to form a diffusable matrix, microcrystalline cellulose (Avicel ® PH-101) in a planetary mixer for 10 minutes at low speed. The blend is then granulated to an extrudable consistency with the addition of water, and the resultant granulate is extruded through a 1.2 to 1.8 mm plate. The resultant extrudate is spheronized at high speed for one to three minutes. The resultant spherical granules are dried in a fluid bed dryer at 65° C.–70° C. until the moisture content is about 3 to 5 percent to form compressible spherical granules.

A blend of 25 parts (0.1 gm) of the active spherical granules containing 50 mg of active medicament, 74.9 parts (0.2996 gm) of the compressible spherical granules, and 0.1 part (0.0004 gm) of lubricant is compressed into a tablet.

Microscopic examination of the tablet reveals a uniform distribution of substantially unbroken active spherical granules throughout.

A dissolution profile of the active medicament is determined by U.S.P. XXI test methods using a dissolution medium with a pH of 4.5 and an acetate buffer and stirring with paddles. The results appear in FIG. 13 in graph form.

EXAMPLE 15

The procedure of Example 14 is followed substituting 0.6 to 0.8 mm plates for the extruder plates. A dissolution profile is determined. The results appear in FIG. 13 in graph form.

EXAMPLE 16

The procedure of Example 14 is followed substituting plates with openings of less than 0.6 mm for the extruder plates. A dissolution profile is determined. The results appear in FIG. 13 in graph form.

Examples 12 and 14–16 indicate that spherical granule diameters can be manipulated to provide different controlled release rates.

EXAMPLE 17

A blend of 25 parts (0.1 gm) of active spherical granules prepared by the procedure of Example 2 containing 50 mg of active medicament, 74.9 parts (0.2996 gm) of compressible spherical granules prepared by the procedure of Example 8, and 0.1 part (0.0004 gm) of lubricant is compressed into a tablet to a hardness of 5–10 kilopascals (kp).

Microscopic examination of the tablet reveals a uniform distribution of substantially unbroken active spherical granules throughout.

A dissolution profile of the active medicament in the untabletted active spherical granules is determined by U.S.P. XXI test methods using a dissolution medium with a pH of 4.5 and an acetate buffer and stirring with paddles. The result appears in FIG. 14 in graph form.

A dissolution profile of the tabletted oral dosage unit form is determined as above. The result appears in FIG. 15 in graph form.

EXAMPLE 18

A blend of 25 parts (0.1 gm) of active spherical granules prepared by the procedure of Example 3 containing 50 mg of active medicament, 74.9 parts (0.2996 gm) of compressible spherical granules prepared by the procedure of Example 8, and 0.1 part (0.0004 gm) of lubricant is compressed into a tablet to a hardness of 5-10 kp.

Microscopic examination of the tablet reveals a uniform distribution of substantially unbroken active spherical granules throughout.

A dissolution profile of the active medicament in the untabletted active spherical granules is determined by U.S.P. XXI test methods using a dissolution medium with a pH of 4.5 and an acetate buffer and stirring with paddles. The result appears in FIG. 14 in graph form.

EXAMPLE 19

A blend of 25 parts (0.1 gm) of active spherical granules prepared by the procedure of Example 4 containing 50 mg of active medicament, 74.9 parts (0.2996 gm) of compressible spherical granules prepared by the procedure of Example 8, and 0.1 part (0.0004 gm) of lubricant is compressed into a tablet to a hardness of 5-10 kp.

Microscopic examination of the tablet reveals a uniform distribution of substantially unbroken active spherical granules throughout.

A dissolution profile of the active medicament in the tabletted active spherical granules is determined by U.S.P. XXI test methods using a dissolution medium with a pH of 4.5 and an acetate buffer and stirring with paddles. The result appears in FIG. 14 in graph form.

A dissolution profile of the tabletted oral dosage unit form is determined as above. The result appears in FIG. 15 in graph form.

Figure 14:
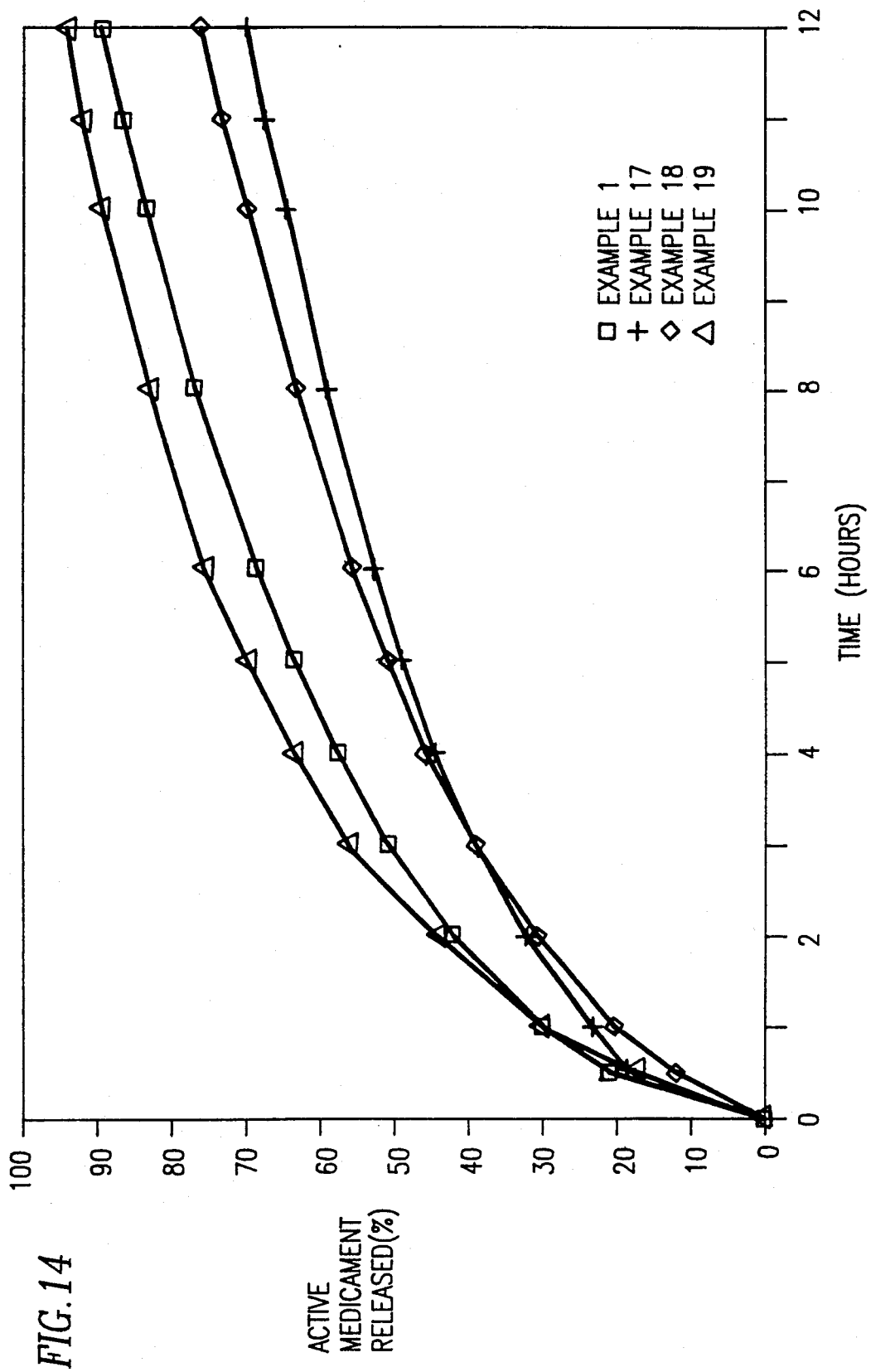
FIG. 14 is a graphic illustration of the effect of the amount of Neptazane ® present in bare active spherical granules (untabletted form) on the dissolution rate of active medicament.
Figure 15:
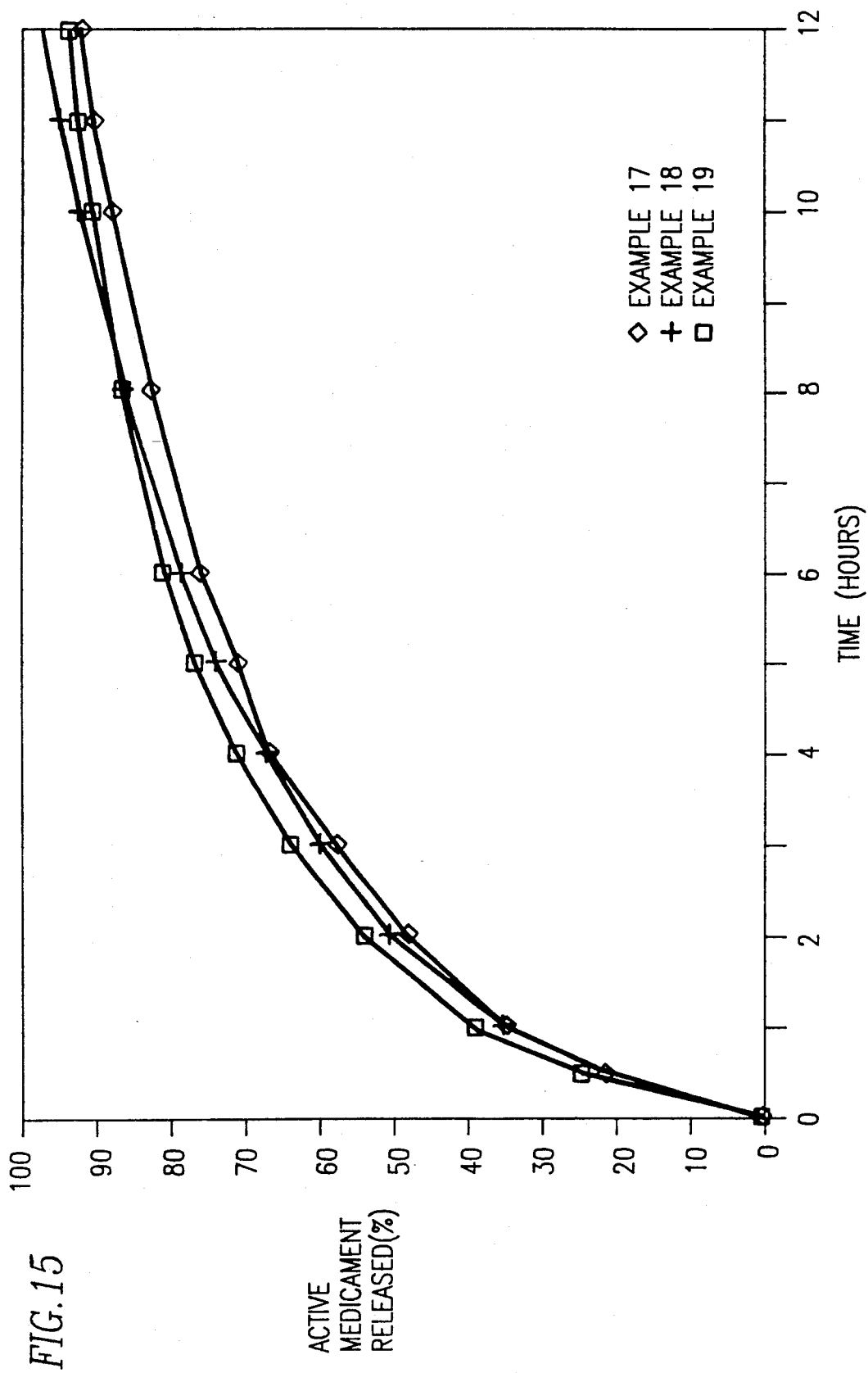
FIG. 15 is a graphic illustration of the effect of the amount of Neptazane ® present in active spherical granules formulated into oral dosage unit forms of the present invention on the dissolution rate of the Neptazane ®.

Examples 17-19 and FIGS. 14 and 15 demonstrate that a broad range of active medicament loadings can be delivered effectively from tablets according to the present invention when the tablets are compressed to the same hardness.

The above-mentioned patents, publications and test methods are incorporated herein by reference.

Many variations will suggest themselves to those skilled in this art in light of the foregoing detailed description. For example, the tablets of the present invention may comprise fertilizers, pesticides, disinfectants and the like and may be useful in water supplies, swimming pools and the like. Additionally, instead of 7-dimethyl-6-deoxy-6-demethyltetracycline hydrochloride, the free base, the sulfuric acid and the trichloroacetic acid addition salts can be used. Instead of 7-dimethyl-6-deoxy-demethyltetracycline hydrochloride, the hydrochlorides of the following compounds can be used: 7-methylamino-6-deoxy-6-demethyltetracycline; 9-methylamino-6-deoxy-6-demethyltetracycline; 7-ethylamino-6-deoxy-6-demethyltetracycline; and 7-isopropylamino-6-deoxydemethyltetracycline. As a film former, ethyl cellulose can be used alone. All such obvious variations are within the full intended scope of the appended claims.

We claim:

1. A controlled release pharmaceutical composition in oral dosage unit form comprising a table comprising
   (A) a therapeutically effective number of active spherical granules comprising
      (i) about 10 to about 80 parts by weight of at least one active medicament;
      (ii) about 75 to about 10 parts by weight of microcrystalline cellulose for controlling the release rate of said at least one active medicament (A) (i); and,
      (iii) 10 to about 75 parts by weight of at least one pharmaceutically acceptable excipient for further controlling the release rate of said at least one active medicament (A) (i), based upon 100 parts by weight of said active spherical granules; and
   (B) a number of compressible spherical granules comprising
      (i) about 25 to about 90 parts by weight of at least one mono- or di-saccharide; optionally,
      (ii) 75 to about 10 parts by weight of microcrystalline cellulose for controlling the release rate of any active medicament in said compressible spherical granules; optionally,
      (iii) an effective amount of at least one active medicament which may be the same as or different than (A) Ii); optionally
      (iv) 0 to about 90 parts by weight of at least one pharmaceutically acceptable excipient other than a mono- or di-saccharide which may be the same or different than either (A) (ii), (A) (iii) or (B) (ii) for further controlling the release rate of any active medicament in said compressible spherical granules; or optionally
      (v) a combination of any of (B) (ii), (B) (iii) and (B) (iv), based upon 100 parts by weight of said compressible spherical granules;
   wherein the average compressive yield of component (B) is less than the average compressive yield of component (A).

2. A method for the preparation of a controlled release pharmaceutical composition in oral dosage unit form comprising a tablet comprising the steps of:
   (a) blending
      (i) about 10 to about 80 parts by weight of at least one active medicament;
      (ii) about 75 to about 10 parts by weight of microcrystalline cellulose; and optionally,
      (iii) 10 to about 75 parts by weight of at least one pharmaceutically acceptable excipient based upon 100 parts by weight of (a) (i), (a) (ii) and (a) (iii) combined;
   (b) independently blending
      (i) about 25 to about 90 parts by weight of at least one mono- or di-saccharide; optionally,
      (ii) 75 to about 10 parts by weight of microcrystalline cellulose;
      (iii) an effective amount of at least one active medicament which may be the same as or different than (a) (i); optionally
      (iv) 0 to about 90 parts by weight of at least one pharmaceutically acceptable excipient other than a mono- or di saccharide which may be the same or different than either (a) (ii), (a) (iii) or (b) (ii) for further controlling the release rate of any active medicament in said compressible spherical granules; or optionally
      (v) a combination of any of (b) (ii), (b) (iii) and (b) (iv), based upon 100 parts by weight of (b) (i), (b) (ii), and (b) (iii) and (b) (iv) combined;
   (c) independently granulating the resultant blends of steps (a) and (b) in the presence of a granulating liquid;
   (d) independently extruding the resultant granulates of step (c);
   (e) independently spheronizing the resultant extrudates of step (d) to form active spherical granules (A) derived from step (a) and compressible spherical granules (B) derived from step (b) so that the average compressive yield of components (B) is less than the average compressive yield of components (A);

(f) drying components (A) and (B);

(g) optionally adding a lubricant; and (h) forming a tablet from a blend of a therapeutically effective number of active spherical granules (A) and a number of compressible spherical granules (B).

3. A controlled release pharmaceutical composition in oral dosage unit form comprising a compressed tablet consisting essentially of
(A) a therapeutically effective number of active spherical granules which consist essentially of
(i) from about 10 to about 80 parts by weight of at least one active medicament;
(ii) from about 75 to about 10 parts by weight of microcrystalline cellulose for controlling the release rate of said at least one active medicament (A) (i) based on 100 parts by weight of said active spherical granules; and
(B) a number of compressible spherical granules which consists essentially of
(i) about 25 to about 90 parts by weight lactose; and
(ii) from about 75 to about 10 parts by weight of microcrystalline cellulose based on 100 parts by weight of said compressible spherical granules;
wherein prior to tabletting the average compressive yield of component (B) is less than the average compressive yield of component (A).

4. An oral dosage unit as defined in claim 1 wherein said active medicament (A) (i) cellulose in (A) (ii) comprises from about 25 parts to about 65 parts by weight and said excipient (A) (iii) comprises from about 10 to about 50 parts by weight based upon 100 parts by weight of said active spherical granules (A).

5. An oral dosage unit as defined in claim 1 wherein said active medicament (A) (i) comprises from about 120 to about 75 parts by weight and said microcrystalline cellulose comprises from about 75 to about 10 parts by weight based upon 1200 parts by weight of said active spherical granules (A).

6. An oral dosage unit as defined in claim 5 wherein said active medicament (A) (i) comprises about 50 parts by weight and said microcrystalline cellulose comprises about 540 parts by weight based upon 100 parts by weight of said active spherical granules (A).

7. A controlled release pharmaceutical composition in oral dosage unit form comprising a compressed tablet consisting essentially of
(A) a therapeutically effective number of active spherical granules which consist essentially of
(i) about 10 to about 90 parts by weight of at least one active medicament;
(ii) about 90 to about 10 parts by weight of microcrystalline cellulose for controlling the release rate of said at least one active medicament (A) (i), based upon 100 parts by weight of said active spherical granules; and
(B) a number of compressible spherical granules which consist essentially of
(i) about 10 to about 90 parts by weight of lactose; and
(ii) about 90 to about 10 parts by weight of microcrystalline cellulose based upon 100 parts by weight of said compressible spherical granules;
wherein prior to tabletting the average compressive yield of component (B) is less than the average compressive yield of component (A).

8. A controlled release pharmaceutical composition as defined in claim 1 wherein the pharmaceutically acceptable excipient is lactose.

9. An oral dosage unit as defined in claim 1 wherein said mono- or di-saccharide (B) (i) comprises from about 50 to about 90 parts by weight and said microcrystalline cellulose comprises from about 50 to about 10 parts by weight based upon 100 parts by weight of said compressible spherical granules.

10. An oral dosage unit as defined in claim 9 wherein said mono- or di-saccharide (B) (i) comprises about 75 parts by weight and said microcrystalline cellulose comprises about 25 parts by weight based upon 100 parts by weight of said compressible spherical granules (B).

11. An oral dosage unit as defined in claim 1 wherein said active spherical granules (A) comprise from about 10 to about 90 parts by weight and said compressible spherical granules (B) comprise from about 90 to about 10 parts by weight based upon 100 parts by weight of (A) and (B) combined.

12. An oral dosage unit as defined in claim 11 wherein said active spherical granules (A) comprise about 50 parts by weight and said compressible spherical granules (B) comprise about 50 parts by weight based upon 100 parts by weight of (A) and (B) combined.

13. An oral dosage unit form as defined in claim 7 wherein said active medicament (A) (i) is selected from the group consisting of methazolamide, ibuprofen, dipopyramide, and a tetracycline compound.

14. An oral dosage unit form as defined in claim 13 wherein said tetracycline compound is minocycline hydrochloride.

15. A controlled release pharmaceutical composition as defined in claim 1 wherein the pharmaceutically acceptable excipient is selected from the group consisting of lactose, microcrystalline cellulose, polyvinylpyrrolidone, hydroxypropylmethyl cellulose, microcrystalline cellulose and sodium carboxymethyl cellulose and mixtures of the foregoing; the mono- or di-saccharide is lactose and the pharmaceutically acceptable diluent other than a mono- or di-saccharide is microcrystalline cellulose.

16. An oral dosage unit as defined in claim 1 wherein said active medicament (A)(i) comprises methazolamide.

17. An oral dosage unit as defined in claim 16 wherein each tablet contains from about 25 mg to about 75 mg of methazolamide.

18. An oral dosage unit as defined in claim 16 wherein not more than about 50 percent of said methazolamide is released from said active spherical granules (A) in about one hour and not less than about 75 percent of said methazolamide is released from said active spherical granules in about 12 hours when suspended in pH 4.5 acetate buffer at about 37° C. at a methazolamide concentration of about 50 mg of methazolamide/90 ml of buffer.

19. An oral dosage unit as defined in claim 1 wherein said active medicament (A)(i) comprises ibuprofen.

20. An oral dosage unit as defined in claim 19 where each tablet contains from about 200 mg to about 800 mg of ibuprofen.

21. An oral dosage unit as defined in claim 19 wherein not more than about 60 percent of said ibuprofen is released from said active spherical granules (A) in about one hour and not less than about 90 percent of said ibuprofen is released in about 8 hours when suspended in pH 7.2 phosphate buffer at about 37° C. at an ibuprofen concentration of about 800 mg of ibuprofen/900 ml of buffer.

22. An oral dosage unit as defined in claim 1 wherein said active medicament (A)(i) comprises disopyramide phosphate.

23. An oral dosage unit as defined in claim 22 wherein each tablet contains from about 100 mg to about 300 mg of disopyramide phosphate.

24. An oral dosage unit as defined in claim 22 wherein 5 to 25 percent of said disopyramide phosphate is released from said active spherical granules (A) in about 1 hour, 17 to 43 percent of said disopyramide phosphate is released from said active spherical granules (A) in about 2 hours, 50 to 80 percent of said disopyramide phosphate is released from said active spherical granules (A) in about 5 hours and not less than 85 percent of said disopyramide phosphate is released from said active spherical granules (A) in about 12 hours when suspended in pH 2.5 phosphate buffer at about 37° C. at a disopyramide phosphate concentration of from about 100 mg to about 300 mg disopyramide phosphate/900 ml of buffer.

25. An oral dosage unit as defined in claim 1 wherein said active medicament (A)(i) comprises a tetracycline compound.

26. An oral dosage unit as defined in claim 25 wherein each tablet contains from about 25 mg to about 200 mg of tetracycline compound.

27. An oral dosage unit as defined in claim 25 wherein each tablet contains from about 50 mg to about 100 mg of tetracycline compound.

28. An oral dosage unit as defined in claim 25 wherein not more than about 80 percent of said tetracycline compound is released from said active spherical granules (A) in about 1 hour and not less than about 90 percent of said tetracycline compound is released from said active spherical granules (A) in about 12 hours when suspended in deionized water at about 37° C. at a tetracycline compound concentration of about 50 mg to about 100 mg of tetracycline compound/900 ml of water.

29. An oral dosage unit as defined in claim 25 wherein said tetracycline compound comprises minocycline hydrochloride.

30. An oral dosage unit as defined in claim 29 wherein each tablet contains from about 50 mg to about 100 mg of minocycline hydrochloride.

31. An oral dosage unit as defined in claim 29 wherein not more than about 80 percent of said minocycline hydrochloride is released from said active spherical granules (A) in about 1 hour and not less than about 90 percent of said minocycline hydrochloride is released from said active spherical granules (A) in about 12 hours when suspended in deionized water at about 37° C. at a minocycline hydrochloride concentration of about 50 mg to about 200 mg of minocycline hydrochloride/900 ml of water.

32. A method of controlling the release of at least one active medicament in the blood stream of a warm-blooded mammal over a prolonged period of time comprising the ingestion of an oral dosage unit as defined in claim 1.

33. An oral dosage unit as defined in claim 1 wherein at least one of said pharmaceutically acceptable excipients (A)(iii) and (B)(iv) comprises microcrystalline cellulose, polyvinylpyrrolidone, hydroxypropylmethyl cellulose, microcrystalline cellulose in combination with lactose, microcrystalline cellulose in combination with sodium carboxymethyl cellulose or a mixture of any of the foregoing.

34. An oral dosage unit as defined in claim 1 wherein said mono- or di-saccharide comprises lactose.

35. An oral dosage unit as defined in claim 1 wherein said active spherical granules (A) and said compressible spherical granules (B) independently have an average diameter in the range of from about 0.1 to about 2.5 millimeters.

36. An oral dosage unit as defined in claim 35 wherein said active spherical granules (A) and said compressible spherical granules (B) independently have an average diameter in the range of from about 0.8 to about 1.2 millimeters.

37. An oral dosage unit as defined in claim 1 wherein said active spherical granules (A), said compressible spherical granules (B), said table or any combination of the foregoing includes a layer of a polymer coating.

38. An oral dosage unit as defined in claim 37 wherein said polymer comprises from about 1 to less than about 25 parts by weight based upon 100 parts by weight of either (A), (B) or the tablet being coated.

39. An oral dosage unit as defined in claim 38 wherein said polymer comprises from about 1 to about 5 percent by weight based upon 100 parts by weight of either (A), (B) or the tablet being coated.

40. An oral dosage unit as defined in claim 38 wherein said polymer is selected from
 (a) methylcellulose;
 (b) ethylcellulose;
 (c) hydroxyethyl cellulose;
 (d) hydroxypropyl cellulose;
 (e) hydroxypropyl methylcellulose;
 (f) hydroxypropyl methylcellulose phthalate;
 (g) cellulose acetate phthalate;
 (h) hydroxypropyl methylcellulose succinate;
 (i) a polymer or copolymer of (meth)acrylic acid or an ester thereof; or
 (j) a mixture of any of the foregoing, alone, or in further combination with a plasticizer, a colorant or a pigment.

41. An oral dosage unit as defined in claim 1 which also includes a top coating layer of the same or a different polymer over an intermediate polymer coating layer.

42. An oral dosage unit as defined in claim 41 wherein said intermediate layer and said top layer comprise hydroxypropyl methylcellulose.

43. An oral dosage unit as defined in claim 1 wherein said therapeutically effective number of active spherical granules (A) comprise a mixture of
 (A-1) a therapeutically effective number of active spherical granules comprising
  (i) about 10 to about 80 parts by weight of at least one active medicament;
  (ii) about 75 to about 10 parts by weight of microcrystalline cellulose for controlling the release rate of said at least one active medicament (A-1)(i); and,
  (iii) 10 to about 50 parts by weight of at least one pharmaceutically acceptable excipient based upon 100 parts by weight of said active spherical granules (A-1); and
 (A-2) a therapeutically effective number of active spherical granules comprising:

(i) about 10 to about 80 parts by weight of at least one active medicament which is different than (A-1) (i);
(ii) about 75 to about 10 parts by weight of microcrystalline cellulose; and, optionally,
(iii) 10 to about 50 parts by weight of at least one pharmaceutically acceptable excipient based upon 100 parts by weight of said active spherical granules (A-2).

44. An oral dosage unit as defined in claim 1 which is scored.

45. An oral dosage unit as defined in claim 1 which also includes
(C) a lubricant;
(D) a disintegrant;
(E) a plasticizer;
(F) a colorant;
(G) a pigment;
(H) a flavoring;
(I) an active medicament which is the same as or different than either (A)(i) or (B)(iii); or
(J) a combination of any of the foregoing.

* * * * *